United States Patent
Abdolmanafi et al.

(10) Patent No.: US 12,042,247 B2
(45) Date of Patent: Jul. 23, 2024

(54) SYSTEM AND METHOD FOR DETERMINING CORONARY ARTERY TISSUE TYPE BASED ON AN OCT IMAGE AND USING TRAINED ENGINES

(71) Applicants: SOCOVAR, SOCIETE EN COMMANDITE, Montreal (CA); Nagib Dahdah, Ville Mont-Royal (CA); Farida Cheriet, Montréal (CA)

(72) Inventors: Atefeh Abdolmanafi, Montréal (CA); Luc Duong, Verdun (CA); Nagib Dahdah, Ville Mont-Royal (CA); Farida Cheriet, Montréal (CA)

(73) Assignee: ÉCOLE DE TECHNOLOGIE SUPERIEURE, Montreal (CA)

( * ) Notice: Subject to any disclaimer, the term of this patent is extended or adjusted under 35 U.S.C. 154(b) by 816 days.

(21) Appl. No.: 17/251,306

(22) PCT Filed: Jun. 11, 2019

(86) PCT No.: PCT/CA2019/050820
§ 371 (c)(1),
(2) Date: Dec. 11, 2020

(87) PCT Pub. No.: WO2019/237191
PCT Pub. Date: Dec. 19, 2019

(65) Prior Publication Data
US 2021/0251490 A1 Aug. 19, 2021

Related U.S. Application Data

(60) Provisional application No. 62/821,590, filed on Mar. 21, 2019, provisional application No. 62/683,176, filed on Jun. 11, 2018.

(51) Int. Cl.
*A61B 5/00* (2006.01)
*G06F 18/21* (2023.01)
(Continued)

(52) U.S. Cl.
CPC .......... *A61B 5/0066* (2013.01); *A61B 5/0044* (2013.01); *A61B 5/7267* (2013.01);
(Continued)

(58) Field of Classification Search
CPC ... A61B 5/0066; A61B 5/7267; A61B 5/0044; G06T 2207/10101; G06T 2207/20081;
(Continued)

(56) References Cited

U.S. PATENT DOCUMENTS

2003/0172043 A1    9/2003   Guyon et al.
2016/0171711 A1*   6/2016   Gopinath ................ G06T 19/20
                                                       382/130
(Continued)

FOREIGN PATENT DOCUMENTS

CN     107993221 A    5/2018
WO    2009149131 A1   12/2009

OTHER PUBLICATIONS

Abdolmanafi et al (Deep feature learning for automatic tissue classification of coronary artery using optical coherence tomography) (Year: 2017).*

*Primary Examiner* — Joel F Brutus
(74) *Attorney, Agent, or Firm* — Reno Lessard; Norton Rose Fulbright Canada LLP

(57) ABSTRACT

There is described a system for determining a coronal artery tissue type. The system generally has an optical coherence tomography (OCT) imaging system being configured for acquiring an OCT image of coronal artery tissue; and a controller configured to perform the steps of: using trained feature extraction engines, extracting corresponding feature vectors comprising a plurality of features in at least a region of interest of the OCT image; using trained classification engines, determining corresponding preliminary coronal artery tissue types associated to the region of interest of the
(Continued)

OCT image based on corresponding ones of the plurality of feature vectors; and using a majority voting engine, majority voting an output coronal artery tissue type associated to the region of interest of the OCT image based on the previously determined preliminary coronal artery tissue types.

20 Claims, 16 Drawing Sheets

(51) Int. Cl.
| | |
|---|---|
| *G06F 18/2413* | (2023.01) |
| *G06F 18/243* | (2023.01) |
| *G06N 3/08* | (2023.01) |
| *G06T 7/00* | (2017.01) |
| *G06V 10/44* | (2022.01) |
| *G06V 10/764* | (2022.01) |
| *G06V 10/82* | (2022.01) |
| *G16H 30/20* | (2018.01) |

(52) U.S. Cl.
CPC .......... *G06F 18/21* (2023.01); *G06F 18/2413* (2023.01); *G06F 18/24323* (2023.01); *G06N 3/08* (2013.01); *G06T 7/0012* (2013.01); *G06V 10/454* (2022.01); *G06V 10/764* (2022.01); *G06V 10/82* (2022.01); *G16H 30/20* (2018.01); *A61B 5/0084* (2013.01); *A61B 2576/023* (2013.01); *G06T 2207/10101* (2013.01); *G06T 2207/20081* (2013.01); *G06T 2207/20084* (2013.01); *G06T 2207/30048* (2013.01); *G06T 2207/30101* (2013.01); *G06V 2201/03* (2022.01)

(58) Field of Classification Search
CPC . G06T 2207/20084; G06T 2207/40048; G06T 2207/30101
See application file for complete search history.

(56) References Cited

U.S. PATENT DOCUMENTS

2018/0218502 A1\* 8/2018 Golden ..................... G06T 7/11
2018/0247195 A1\* 8/2018 Kumar .................. G16B 40/10

\* cited by examiner

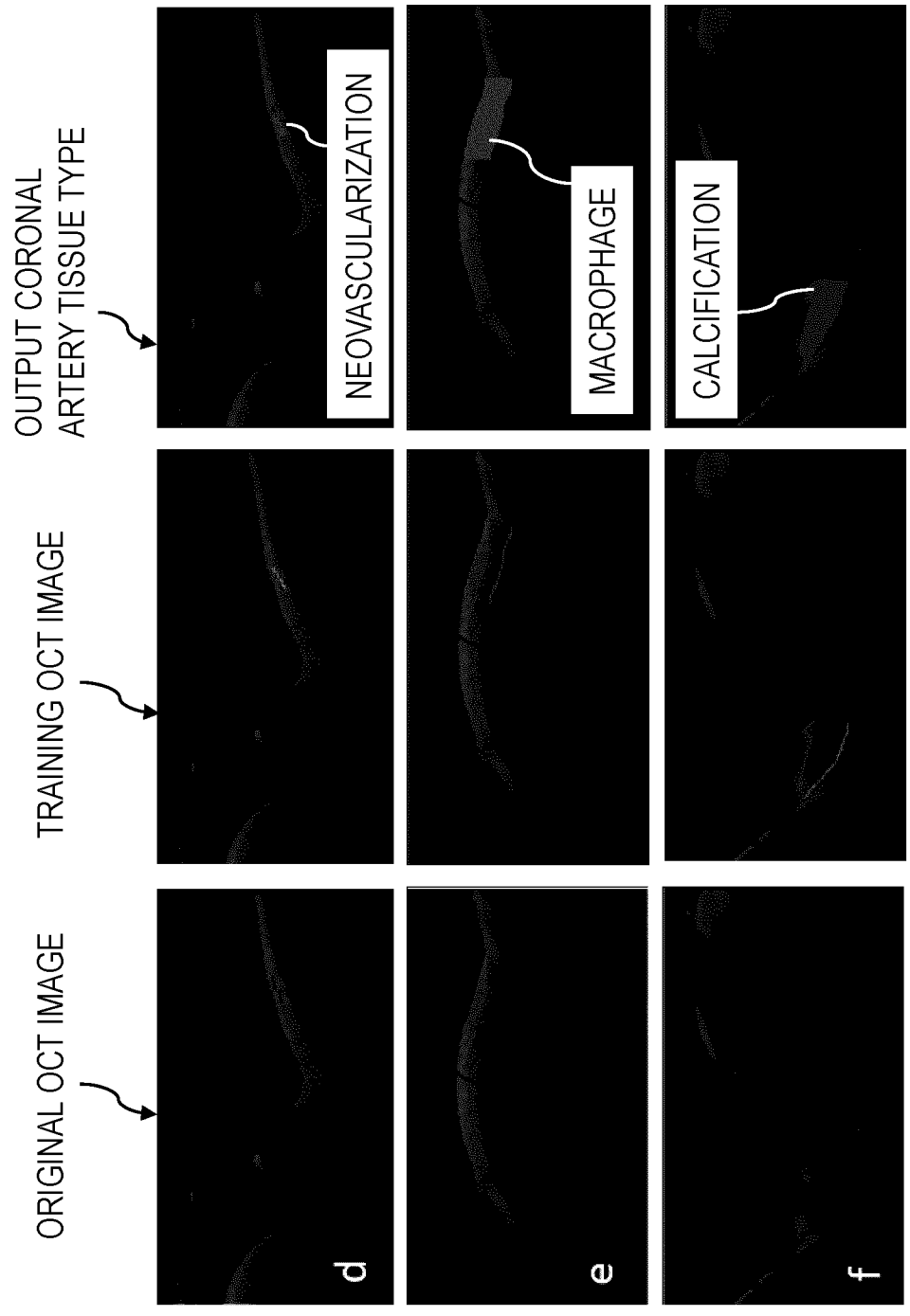

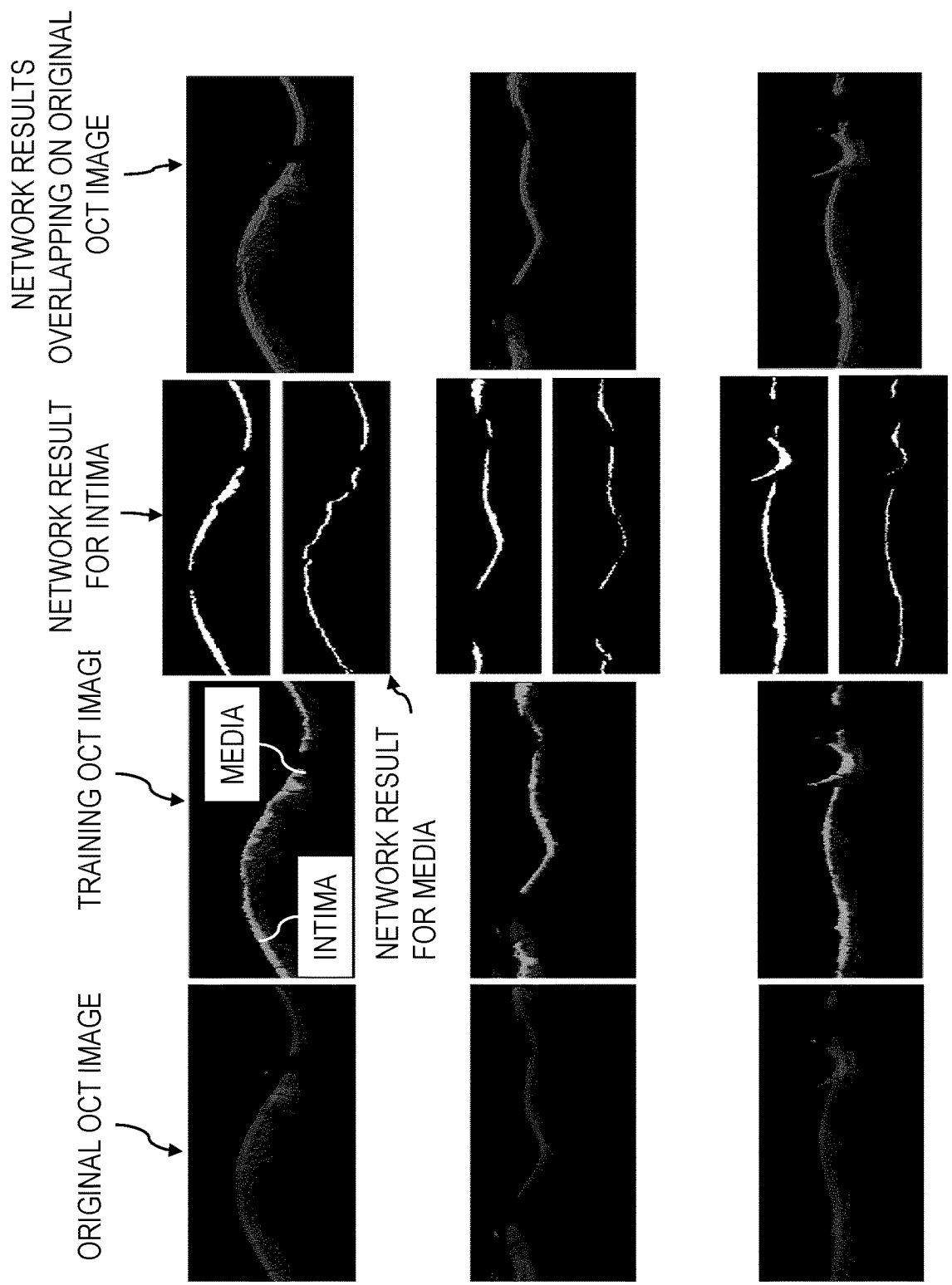

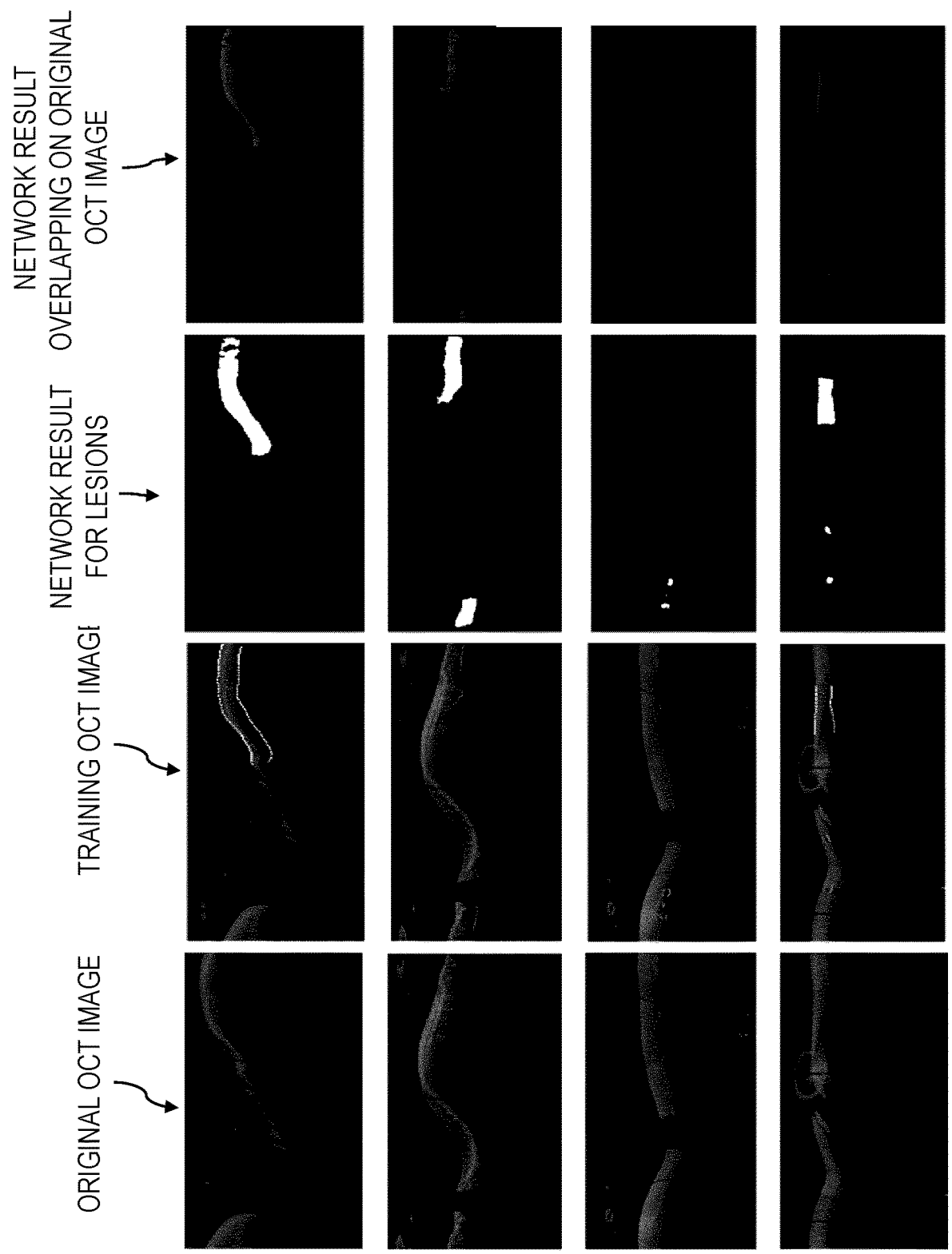

SYSTEM AND METHOD FOR DETERMINING CORONARY ARTERY TISSUE TYPE BASED ON AN OCT IMAGE AND USING TRAINED ENGINES

CROSS-REFERENCE TO RELATED APPLICATIONS

This application claims priority on both U.S. Provisional Application Ser. No. 62/683,176, filed on Jun. 11, 2018, and U.S. Provisional Application Ser. No. 62/821,590, filed on Mar. 21, 2019, the entire contents of which are hereby incorporated by reference.

FIELD

The present disclosure generally relates to the field of coronary artery tissue type determination, and more specifically involves artificial intelligence for said determination.

BACKGROUND

Optical coherence tomography (OCT) imaging techniques involve the use of coherent light which can penetrate well into coronal artery tissues, thus allowing not only an inside wall of the coronal artery to be imaged, but also allowing imaging of deeper layers of the coronal artery.

Although existing OCT imaging techniques are satisfactory to a certain degree, there remains room for improvement. For instance, as acquiring a multitude of OCT images of coronal artery tissue of a patient can be relatively straightforward using existing OCT imaging systems, examining these OCT images can require a significant amount of time from highly qualified physicians.

SUMMARY

It is an aim of the present disclosure to describe methods and systems suited for determining a tissue type associated to coronal artery tissue in at least one region of interest of an OCT image using computer-implemented trained engines.

In accordance with a first embodiment of the present disclosure, there is provided a system for determining a coronal artery tissue type, the system comprising: an optical coherence tomography (OCT) imaging system being configured for acquiring an OCT image of coronal artery tissue; and a controller having a memory and a processor configured to perform the steps of: accessing the acquired OCT image; using a plurality of different feature extraction engines each being stored on the memory and being trained, extracting a corresponding plurality of different feature vectors comprising a plurality of features in at least a region of interest of the OCT image; using a plurality of classification engines each being stored on the memory and being trained, determining a corresponding plurality of preliminary coronal artery tissue types associated to the region of interest of the OCT image based on corresponding ones of the plurality of different feature vectors; using a majority voting engine stored on the memory and being trained, majority voting an output coronal artery tissue type associated to the region of interest of the OCT image based on the previously determined plurality of preliminary coronal artery tissue types; and outputting the output coronal artery tissue type. In some embodiments, at least one of the feature extraction engines has a fully convolutional network (FCN) architecture. The FCN architectures may be different from one another, from one feature extraction engine to another.

In some other embodiments, at least one of the plurality of feature extraction engines has a convolutional neural network (CNN) architecture. In some embodiments, combination of FCN and CNN architectures can also be used.

Further in accordance with the first embodiment, at least one of the plurality of different feature extraction engines for example has a fully convolutional network (FCN) architecture.

Still further in accordance with the first embodiment, at least one of the plurality of different feature extraction engines for example has a convolutional neural network (CNN) architecture.

Still further in accordance with the first embodiment, the CNN architecture of the one of the feature extraction engines is for example selected in the group consisting of: a simple architecture network, a deep architecture network and a complex architecture network.

Still further in accordance with the first embodiment, the plurality of different feature extraction engines comprises for example a first feature extraction engine being stored on the memory and being trained, the first feature extraction engine being configured for extracting a first feature vector comprising a first plurality of features in the region of interest of the OCT image; a second feature extraction engine being stored on the memory and being trained, the second feature extraction engine being configured for extracting a second feature vector comprising a second plurality of features in the region of interest of the OCT image; a third feature extraction engine being stored on the memory and being trained, the third feature extraction engine being configured for extracting a third feature vector comprising a third plurality of features in the region of interest of the OCT image; the first feature extraction engine having a first architecture network, the second feature extraction engine having a second architecture network and the third feature extraction engine having a third architecture network, the first, second and third architecture networks being different from one another.

Still further in accordance with the first embodiment, the first architecture network is for example provided in the form of an AlexNet simple architecture network, the second architecture network is for example provided in the form of a Vgg-19 deep architecture network and the third architecture network is for example provided in the form of an Inception-v3 complex architecture network.

Still further in accordance with the first embodiment, the plurality of classification engines for example comprises: a first classification engine being stored on the memory and being trained, the first classification engine having been trained using feature vectors extracted using the first feature extraction engine; a second classification engine being stored on the memory and being trained, the second classification engine having been trained using feature vectors extracted using the second feature extraction engine; a third classification engine being stored on the memory and being trained, the third classification engine having been trained using feature vectors extracted using the third feature extraction engine.

Still further in accordance with the first embodiment, the plurality of classification engines are for example provided in the form of Random Forest classification engines.

Still further in accordance with the first embodiment, the plurality of classification engines have been trained for example using supervised learning during which each classification engine is trained to determine a preliminary coronal artery tissue type in a plurality of training OCT images each showing different coronal artery tissue types and having truth tissue type associated to each of the training OCT images.

Still further in accordance with the first embodiment, the majority voting engine is for example configured to provide an output indicating the output coronal artery tissue type on the accessed OCT image, the output comprising overlaying at least one text string indicative of the determined output coronal artery tissue type on the accessed OCT image.

Still further in accordance with the first embodiment, an image conversion engine is stored on the memory and is for example configured to convert the OCT image from a Cartesian representation to a polar representation.

Still further in accordance with the first embodiment, the output coronal artery tissue type is for example one of intima, media, adventitia, calcification, fibrosis, macrophage, neovascularization and scar.

Still further in accordance with the first embodiment, an abnormality assessment engine is for example configured to assess an abnormality associated to the region of interest of the accessed OCT image based on the determined output coronal artery tissue type.

Still further in accordance with the first embodiment, the abnormality is for example one of coronary artery aneurysm, intima thickening, media border disappearance, thrombi and stenosis.

In accordance with a second embodiment of the present disclosure, there is provided a computer-implemented method for determining a coronal artery tissue type, the method comprising: using a controller having a memory and a processor: receiving an OCT image of coronal artery tissue; accessing the OCT image; using a plurality of different feature extraction engines each being stored on the memory and being trained, extracting a corresponding plurality of different feature vectors comprising a plurality of features in at least a region of interest of the OCT image; using a plurality of classification engines each being stored on the memory and being trained, determining a corresponding plurality of preliminary coronal artery tissue types associated to the region of interest of the OCT image based on corresponding ones of the plurality of different feature vectors; using a majority voting engine stored on the memory and being trained, majority voting an output coronal artery tissue type associated to the region of interest of the OCT image based on the previously determined plurality of preliminary coronal artery tissue types; and outputting the output coronal artery tissue type. In some embodiments, at least one of the feature extraction engines has a fully convolutional network (FCN) architecture. The FCN architectures may be different from one another, from one feature extraction engine to another. In some other embodiments, at least one of the plurality of feature extraction engines has a convolutional neural network (CNN) architecture. In some embodiments, combination of FCN and CNN architectures can also be used.

Further in accordance with the second embodiment, at least one of the plurality of different feature extraction engines has for example a fully convolutional network (FCN) architecture.

Still further in accordance with the second embodiment, at least one of the plurality of different feature extraction engines has for example a convolutional neural network (CNN) architecture.

Still further in accordance with the second embodiment, the CNN architecture of the one of the feature extraction engines is for example selected in the group consisting of: a simple architecture network, a deep architecture network and a complex architecture network.

Still further in accordance with the second embodiment, the plurality of different feature extraction engines for example comprises: a first feature extraction engine being stored on the memory and being trained, the first feature extraction engine being configured for extracting a first feature vector comprising a first plurality of features in the region of interest of the OCT image; a second feature extraction engine being stored on the memory and being trained, the second feature extraction engine being configured for extracting a second feature vector comprising a second plurality of features in the region of interest of the OCT image; a third feature extraction engine being stored on the memory and being trained, the third feature extraction engine being configured for extracting a third feature vector comprising a third plurality of features in the region of interest of the OCT image; the first feature extraction engine having a first architecture network, the second feature extraction engine having a second architecture network and the third feature extraction engine having a third architecture network, the first, second and third architecture networks being different from one another.

Still further in accordance with the second embodiment, the first architecture network is for example provided in the form of an AlexNet simple architecture network, the second architecture network is for example provided in the form of a Vgg-19 deep architecture network and the third architecture network is for example provided in the form of an Inception-v3 complex architecture network.

It will be understood that the expression "computer" as used herein is not to be interpreted in a limiting manner. It is rather used in a broad sense to generally refer to the combination of some form of one or more processing units and some form of memory system accessible by the processing unit(s). Similarly, the expression "controller" as used herein is not to be interpreted in a limiting manner but rather in a general sense of a device, or of a system having more than one device, performing the function(s) of controlling one or more devices such as an electronic device for instance. It will be understood that the various functions of a computer or of a controller can be performed by hardware or by a combination of both hardware and software. For example, hardware can include logic gates included as part of a silicon chip of the processor. Software can be in the form of data such as computer-readable instructions stored in the memory system. With respect to a computer, a controller, a processing unit, or a processor chip, the expression "configured to" relates to the presence of hardware or a combination of hardware and software which is operable to perform the associated functions.

Many further elements and combinations thereof concerning the present improvements will appear to those skilled in the art following a reading of the instant disclosure.

DESCRIPTION OF THE FIGURES

In the figures,

FIGS. 9A-F are OCT images in planar representations including, from left to right, an original OCT image, a training OCT image including manual segmentation (truth type) for a given coronal artery tissue type, and an output coronal artery tissue type for the given coronal artery tissue type, where the given coronal artery
tissue type is intima in FIG. 9A, media in FIG. 9B, fibrosis in FIG. 9C, neovascularization in FIG. 9D, macrophage in FIG. 9E, and calcification in FIG. 9F, in accordance with some embodiments;

FIGS. 17A-C are OCT images in planar representations for three different patients (top to bottom) including, from left to right, an original OCT image, a training OCT image including manual segmentation (truth type) for a given coronal artery tissue type, showing intima and media, an image showing a network result to extract the tissues, and an image showing the network results overlapping on the original OCT image, in accordance with one or more embodiments; and FIGS. 18A-D are OCT images in planar representations for four different patients (top to bottom) including, from left to right, an original OCT image, a training OCT image including manual segmentation (truth type) for a given coronal artery tissue type showing lesions, an image showing a network result to extract the lesions regardless of the tissue type, and an image showing the extraction of all the regions detected as pathological tissues from the original OCT image, in accordance with one or more embodiments.

DETAILED DESCRIPTION

This disclosure describes systems and methods for determining one or more tissue types of one or more coronal artery tissues in one or more regions of interest in an OCT image. In some embodiments, the tissue type of a coronet artery tissue can be intima, media, adventitia, calcification, fibrosis, macrophage, neovascularization, scar and/or any other suitable types of coronal artery tissue.

Figure 1:
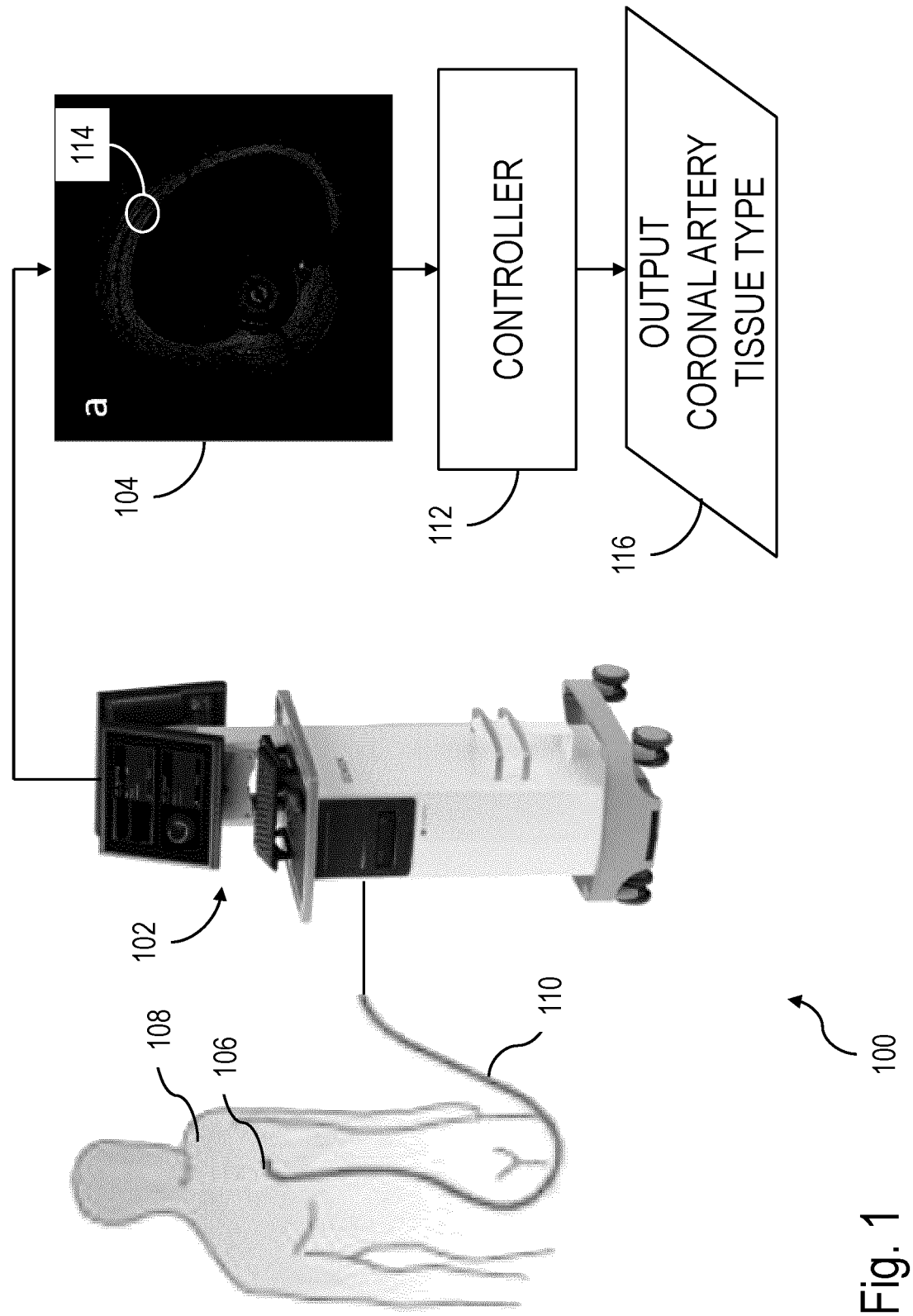
FIG. 1 is a schematic view of an example of a system for determining a coronal artery tissue type, showing an optical coherence tomography (OCT) system and a controller, in accordance with one or more embodiments.

FIG. 1 shows an example of a system 100 for determining a coronal artery tissue type, in accordance with one or more embodiments.

As depicted in this example, the system 100 has an optical coherence tomography (OCT) imaging system 102. As shown, the OCT imaging system 102 is configured for acquiring an OCT image 104 of coronal artery tissue 106 of a patient 108.

Generally, the OCT imaging system 102 has an optical source which is configured to emit an optical signal to be propagated along a waveguide of a guide wire 110 leading to a probe, and an optical detector which is configured to receive a return optical signal from the probe. During use, the probe and a portion of the guide wire 110 are inserted into the coronal artery 106 of the patient 108 for acquiring OCT images 104 of the coronal artery 106. The OCT images 104 can be stored and/or processed within a controller 112 of the OCT imaging system 102 in some embodiments. The controller 112 can have a processing unit, and a non-transitory computer-readable memory communicatively coupled to the processing unit and comprising computer-readable program instructions executable by the processing unit for determining a coronal artery tissue type.

In this specific example, the OCT imaging system 102 is provided in the form of the ILUMIEN OCT imaging system (St. Jude Medical Inc., St. Paul, Minnesota, USA). More specifically, the OCT imaging system 102 has axial and lateral resolutions of 12-15 µm and 20-40 µm, respectively. According to a non-limitative embodiment, OCT image acquisition is performed using frequency domain (FD) OCT with pullback speed of 10 mm/sec and frame rate of 1000 frames/sec. However, depending on the embodiment, any other suitable OCT imaging system can be used.

As shown, the controller 112 is communicatively coupled to the OCT imaging system 102. The communication between the controller 112 and the OCT imaging system 102 can be wired and/or wireless, depending on the embodiment.

As will be described in greater detail below, once an OCT image 104 is acquired by the OCT imaging system 102, the controller 112 is configured for extracting feature vectors each comprising a plurality of features in at least a region of interest 114 of the OCT image 104, using previously trained feature extraction engines. The feature extraction engines can have respective, different convolutional neural network (CNN) architectures so that they can provide different valuable feature information from the OCT image 104. The controller 112 then determines preliminary coronal artery tissue types associated to the region of interest 114 of the OCT image 104 based on corresponding ones of the feature vectors, using trained classification engines. The controller 112 can then, using a majority vote engine, majority vote an output coronal artery tissue type 116 associated to the region of interest 114 of the OCT image based on the previously determined preliminary coronal artery tissue types. Once the output coronal artery tissue type 116 has been determined, the controller 112 can generate a signal indicative of the output coronal artery tissue type 116 for further use.

The controller 112 can be provided as a combination of hardware and software components. The hardware components can be implemented in the form of a computing device 200, an example of which is described with reference to FIG. 2. Moreover, the software components of the controller 112 can be implemented in the form of a software application 300, an example of which is described with reference to FIG. 3.

Figure 2:
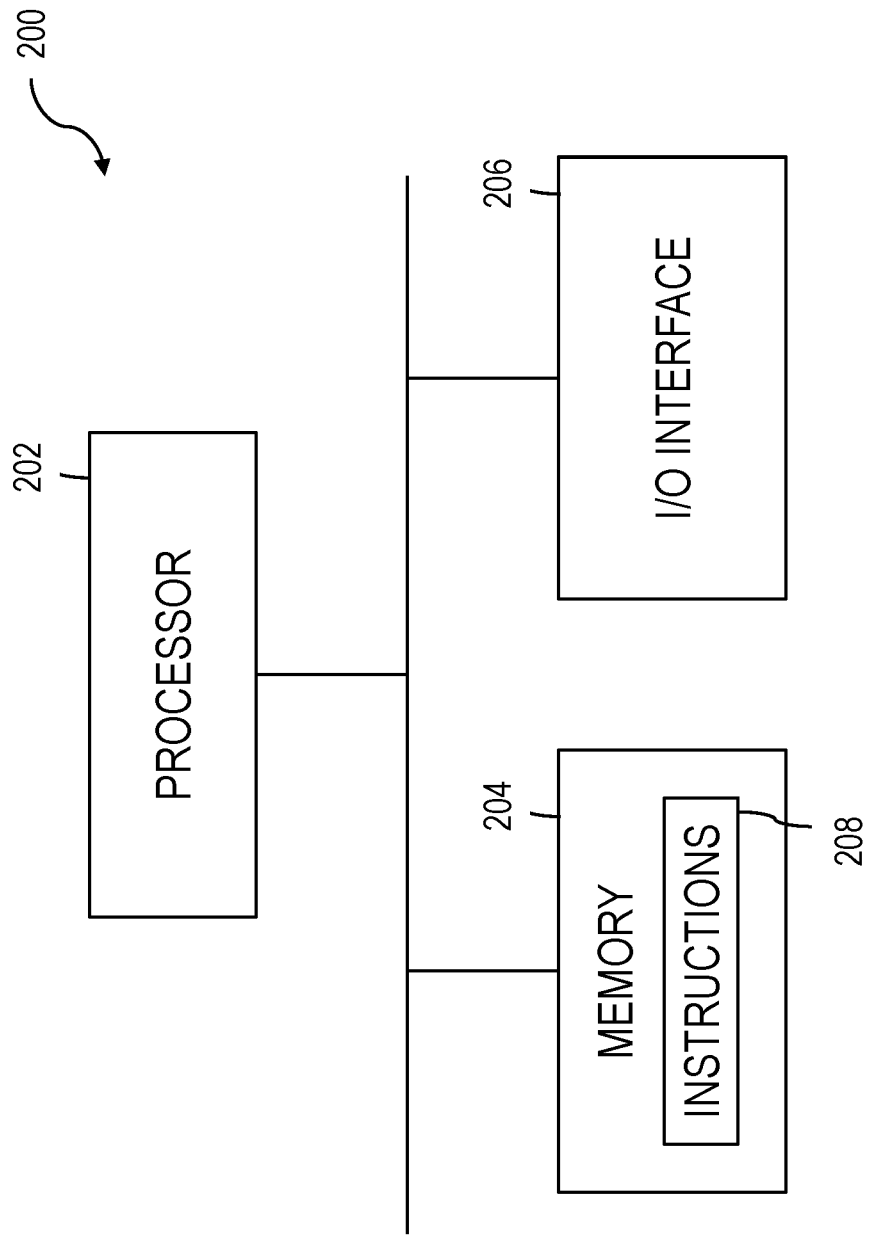
FIG. 2 is a schematic view of an example of a computing device of the controller of FIG. 1, in accordance with one or more embodiments.

Turning now to FIG. 2, the computing device 200 can have a processor 202, a memory 204, and I/O interface 206. Instructions 208 for determining the output coronal artery tissue type can be stored on the memory 204 and accessible by the processor 202.

The processor 202 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 204 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 206 enables the computing device 200 to interconnect with one or more input devices, such as the OCT imaging system 102, or with one or more output devices such as a monitor, a mobile electronic device, a database and the like.

Each I/O interface 206 enables the controller 112 to communicate with other components, to exchange data with other components, to access and connect to network resources, to serve applications, and to perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Figure 3:
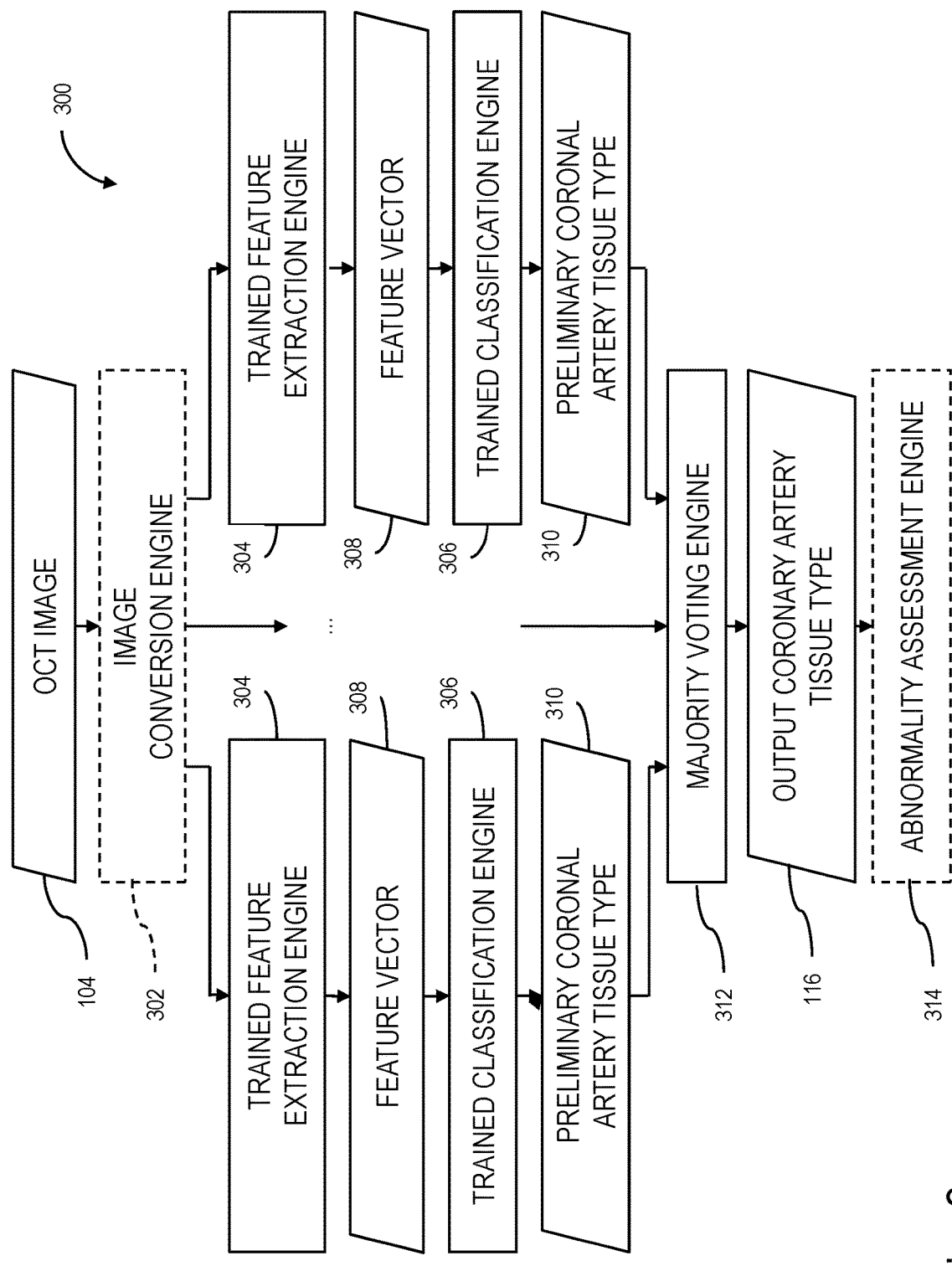
FIG. 3 is a schematic view of an example of a software application of the controller of FIG. 1, in accordance with one or more embodiments.

Referring to FIG. 3, the software application 300 is configured to receive the OCT image 104 and to determine the output coronal artery tissue type 116 associated to the region of interest 114 of the OCT image 104 upon processing the OCT image 104. In some embodiments, the software application 300 is stored on the memory 204 and accessible by the processor 202 of the computing device 200. In the following paragraphs, the software application 300 is in the form of non-transitory computer-readable program instructions that can be executed by the controller 112 and is described with reference to the system 100 of FIG. 1 for ease of reading.

As shown, the software application 300 is configured to access the OCT image 104, which typically shows one or more coronal artery tissues. For instance, the OCT image 104 can be accessed directly from the OCT imaging system 102. Alternately or additionally, the OCT image 104 can be accessed from the memory 204 where the OCT image 104 has been previously stored after its acquisition by the OCT imaging system 102.

As depicted in this specific example, the software application 300 may have an image conversion engine 302 stored on the memory 204 which is configured to convert the OCT image 104 from a Cartesian representation to a polar representation if necessary. Examples of OCT images in a Cartesian representation are shown in FIGS. 4A, 4B, 7A, 7B and 7C whereas examples of OCT images in a polar representation are shown in FIGS. 9A-F.

The software application 300 can also be configured to perform other pre-processing operations such as, but not limited to, recognizing non-tissue elements such as a guide wire, a probe shape, a catheter and/or unwanted blood cells in the OCT image 104. Such pre-processing can also include removing some recognized non-tissue elements.

As depicted, the software application 300 includes a plurality of previously trained feature extraction engines 304, and a corresponding plurality of previously trained classification engines 306. In this example, all the feature extraction engines 304 and the classification engines 306 may be stored on the memory 204 and executable by the processor 202, or may be cloud-based.

It is intended that the feature extraction engines 304 and the classification engines 306 (collectively referred to as the trained engines 304 and 306) can be trained using supervised learning during which the trained engines 304 and 306 are presented with example inputs such as training OCT images and their corresponding desired (or truth) outputs.

More specifically, the software application 300 is configured to perform the step of, using the feature extraction engines 304, extracting a corresponding plurality of feature vectors 308 comprising a plurality of features in at least the region of interest 114 of the OCT image 104.

As discussed above, each of the feature extraction engines 304 can advantageously have respective, different convolutional neural network (CNN) architectures. In some embodiments, the CNN architectures of the feature extraction engines 304 are selected in the group consisting of: a simple architecture network, a deep architecture network and a complex architecture network. Different CNN architectures can allow each of the feature extraction engines 304 to extract different feature vectors 308 from the same OCT image 104. In this way, a given coronal artery tissue type may be better determined using a first feature extraction engine 304 than a different, second feature extraction engine 304, shown as parallel branches in the software application 300.

For instance, the simple architecture network can be provided in the form of an AlexNet simple architecture network in some embodiments. The deep architecture network can be provided in the form of a Vgg-19 deep architecture network in some other embodiments. Additionally or alternately, the complex architecture network can be provided in the form of an Inception-v3 complex architecture network. However, as it will be understood, other combinations of network architecture can also apply.

The number of different feature extraction engines 304 can differ from one embodiment to another. For instance, in an embodiment, the number of different feature extraction engines 304 is three. More specifically, the software application 300 has a first trained feature extraction engine 304 which is configured for extracting a first feature vector comprising a first plurality of features in the region of interest 114 of the OCT image 104. The software application 300 also has a second trained feature extraction engine 304 which is configured for extracting a second feature vector comprising a second plurality of features in the region of interest 114 of the OCT image 104. The software application 300 also has a third trained feature extraction engine 304 which is configured for extracting a third feature vector comprising a third plurality of features in the region of interest 114 of the OCT image 104. In this specific embodiment, the first feature extraction engine has a simple architecture network, the second feature extraction engine has a deep architecture network and the third feature extraction engine has a complex architecture network.

Further, the software application 300 may be configured to perform the step of, using the classification engines 306, determining corresponding preliminary coronal artery tissue types 310 associated to the region of interest 114 of the OCT image 104 based on corresponding ones of the feature vectors 308.

In this specific embodiment, the classification engines 306 are provided in the form of Random Forest classification engines. However, any other suitable classification engine could have alternately been used.

The number of different classification engines 306 can differ from one embodiment to another. For instance, in the preferred embodiment briefly described above, the number of different classification engines 306 is three. More specifically, the software application 300 has a first classification engine 306 which has been trained using feature vectors 308 extracted using the first feature extraction engine 304, a second classification engine 306 which has been trained using feature vectors 308 extracted using the second feature extraction engine 304, and a third classification engine 306 which has been trained using feature vectors 308 extracted using the third feature extraction engine 304. The software application 300 is further configured to perform the step of, using a majority voting engine 312, majority voting an output coronal artery tissue type 116 associated to the region of interest 114 of the OCT image 104 based on the previously determined preliminary coronal artery tissue types 310.

For instance, a first number X1 of the trained classification engines 306 may determine that the coronal artery tissue type associated to a given region of interest of a given OCT image is a first preliminary coronal artery tissue type 310 and a second number X2 of the trained classification engines 306 may determine that the coronal artery tissue type associated to the given region of interest of the given OCT image is a second preliminary coronal artery tissue type 310. In such situations, the majority voting engine 312 can determine that the output coronal artery tissue type is the first preliminary coronal artery tissue type when X1>X2, or alternatively determine that the output coronal artery tissue type is the second preliminary coronal artery tissue type when X2>X1. In some embodiments, X2 may be equal to X1. In such embodiments, the output coronal artery tissue type can be determined based on the complexity of the trained classification engines 306 used to determine the preliminary coronal artery tissue types 310.

By majority voting the output coronal artery tissue type 116 based on the preliminary coronal artery tissue type 310 obtained via the feature vectors 308 extracted from the OCT image 104 using different network architectures, the output coronal artery tissue type 116 may be more accurate, more precise and more specific compared to situations where the output coronal artery tissue type would be any of the preliminary coronal artery tissue types.

In this specific embodiment, the software application 300 may have an abnormality assessment engine 314 which is stored on the memory 204 or cloud-based and which is configured to assess an abnormality associated to the region of interest 114 of the accessed OCT image 104 based on the determined output coronal artery tissue type 116. For instance, examples of such abnormality include coronary artery aneurysms, intima thickening, media border disappearance, thrombi, stenosis and any other suitable coronal artery abnormalities. However, the abnormality assessment engine 314 can be omitted in some embodiments.

Figure 4A:
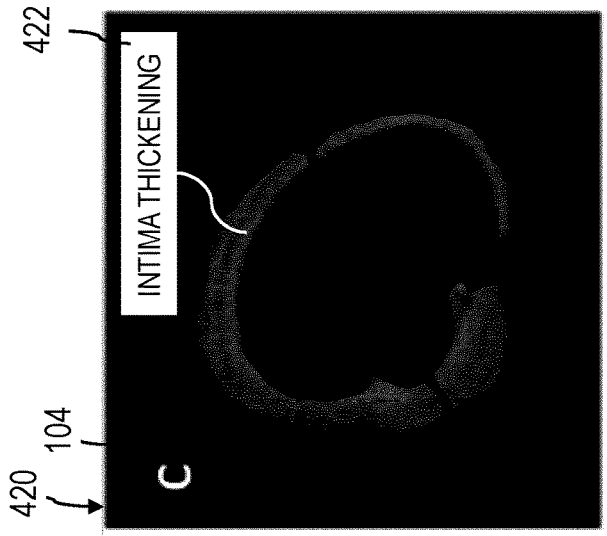
FIG. 4A is an example of an output of the system of FIG. 1, showing an OCT image on which is overlaid a text string being indicative of the output coronal artery tissue type of a region of interest of the OCT image, in accordance with one or more embodiments.
Figure 4B:
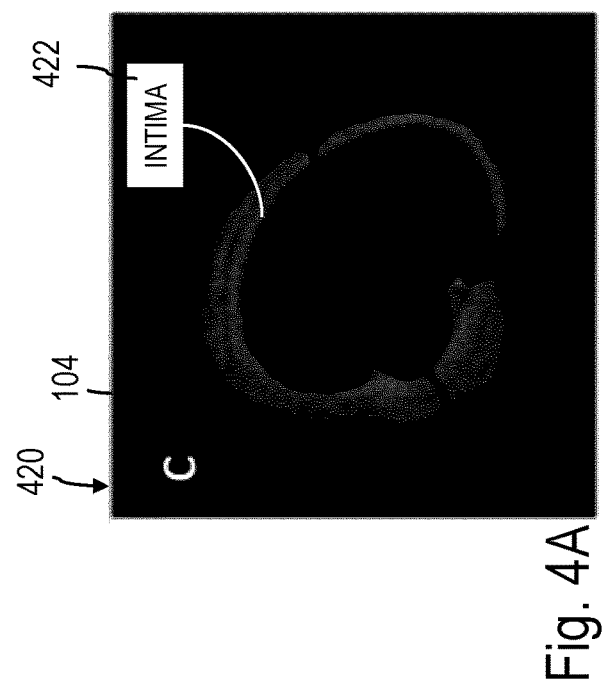
FIG. 4B is an example of an output of the system of FIG. 1, showing an OCT image on which is overlaid a text string being indicative of an abnormality associated to a region of interest of the OCT image, in accordance with one or more embodiments.

In some embodiments, the majority voting engine 312 can be configured to provide an output indicating the output coronal artery tissue type on the accessed OCT image. For instance, in these embodiments, the output comprises overlaying at least one text string indicative of the determined output coronal artery tissue type 116 on the accessed OCT image 104. As such, FIG. 4A shows an OCT image 104 onto which a text string 422 indicating the determined output coronal artery tissue type 116 has been overlaid. Similarly, FIG. 4B shows an OCT image 104 onto which a text string 422 indicating an abnormality of the coronal artery tissue has been overlaid.

Figure 5:
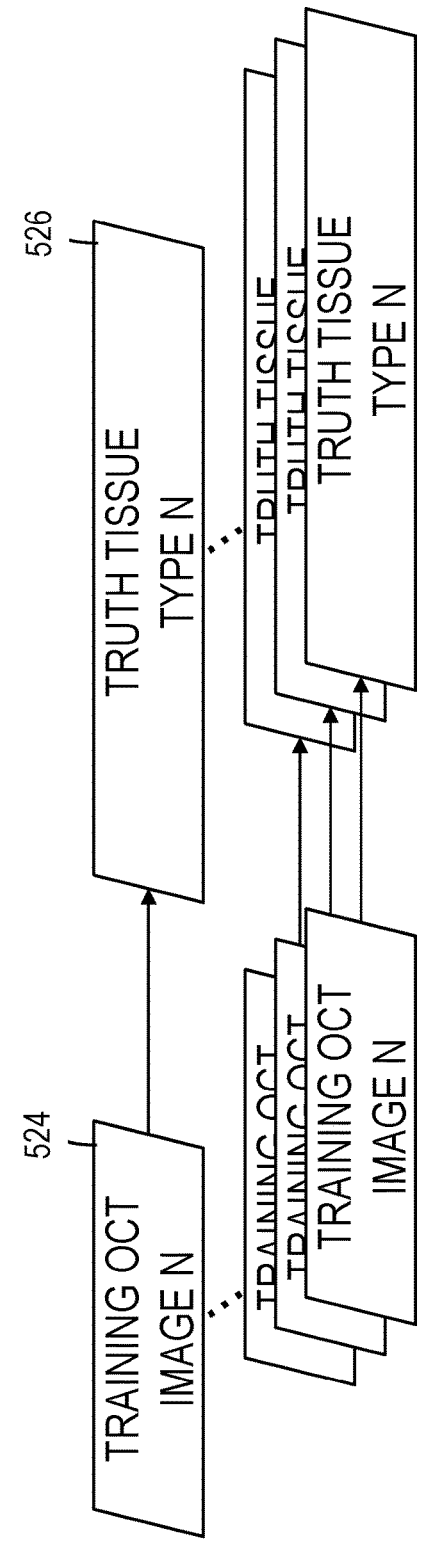
FIG. 5 is a schematic view of exemplary training OCT images and associated truth tissue types, in accordance with one or more embodiments.

As can be understood, in this example, the classification engines 306 have been trained using supervised learning during which the classification engines 306 are trained to determine a preliminary coronal artery tissue type 310 in a plurality of training OCT images each showing different coronal artery tissue types and having truth tissue type associated to each of the training OCT images. Example of training OCT images 524 and their associated truth tissue type 526 are shown in FIG. 5.

The computing device 200 and the software application 300 described above are meant to be examples only. Other suitable embodiments of the controller 112 can also be provided, as it will be apparent to the skilled reader.

Indeed, as mentioned above, the trained engines 304 and 306 are trained using supervised learning. In such supervised learning, each training OCT image 524 in the set of training images may be associated with a label while training. Supervised machine learning engines can be based on Artificial Neural Networks (ANN), Support Vector Machines (SVM), capsule-based networks, Linear Discriminant Analysis (LDA), classification tree, a combination thereof, and any other suitable supervised machine learning engine. However, as can be understood, in some other embodiments, it is intended that the trained engines 304 and 306 be trained using unsupervised learning where only training OCT images 524 are provided (no desired or truth outputs are given), so as to leave the trained engines 304 and 306 find a structure or resemblances in the provided training OCT images 524. For instance, unsupervised clustering algorithms can be used. Additionally or alternatively, the trained engines 304 and 306 can involve reinforcement learning where the trained engines 304 and 306 interact with example training images. Accordingly, when they reach desired or truth outputs, the trained engines 304 and 306 receive feedback in terms of rewards or punishments. Two exemplary methods for improving classifier performance include boosting and bagging, which involve using several classifiers together to "vote" for a final decision. Combination rules can include voting, decision trees, and linear and nonlinear combinations of classifier outputs. These approaches can also provide the ability to control the tradeoff between precision and accuracy through changes in weights or thresholds. These methods can lend themselves to extension to large numbers of localized features. In any case, some of these engines may require human interaction during training, or to initiate the engine, however human interaction may not be required while the engine is being carried out, e.g., during analysis of an accessed image. See Nasrabadi, Nasser M. "Pattern recognition and machine learning." Journal of electronic imaging 16.4 (2007): 049901 for further details concerning such trained engines 304 and 306.

Figure 6:
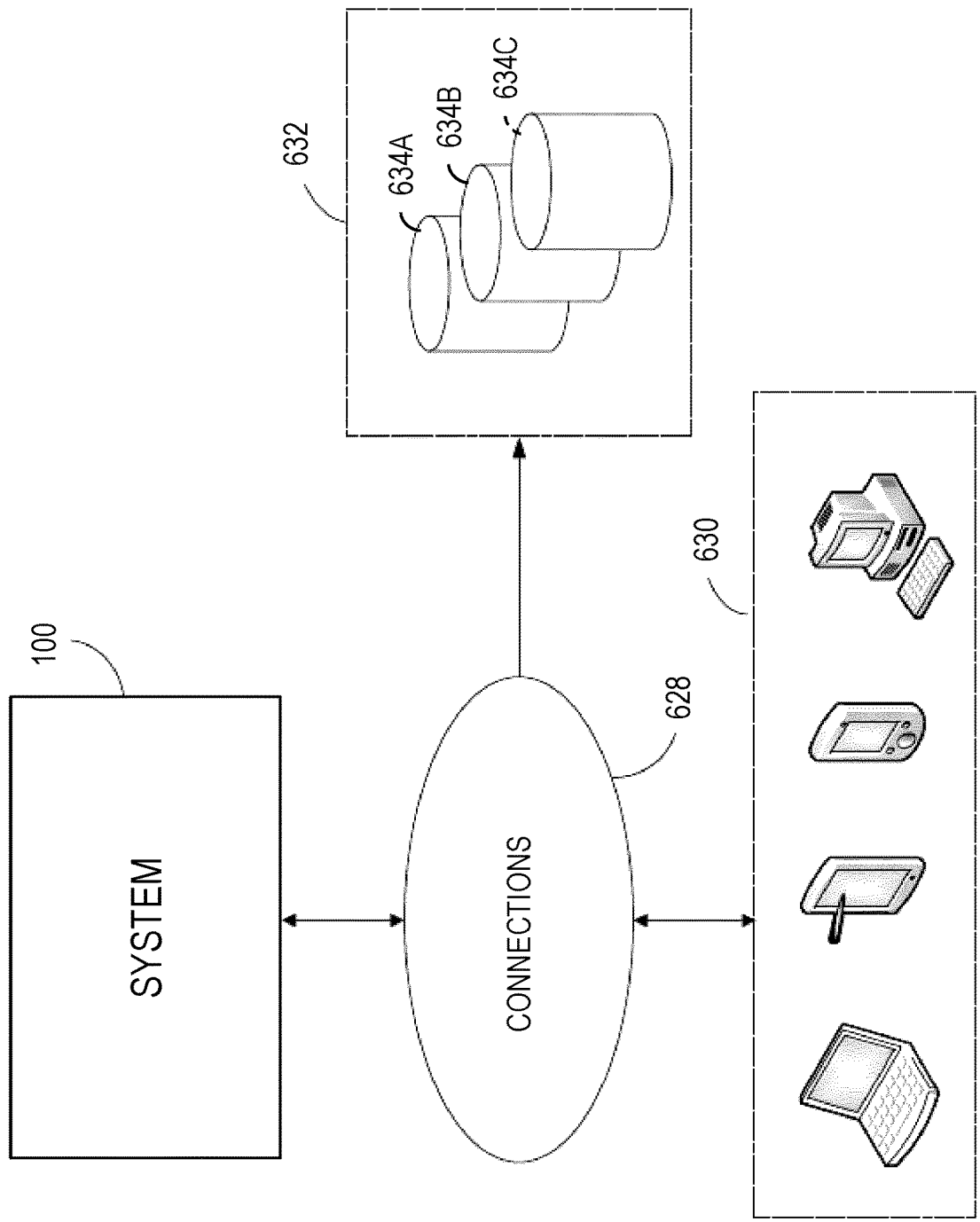
FIG. 6 is a block diagram illustrating an exemplary system incorporating the system of FIG. 1 via network(s) and connection(s), in accordance with one or more embodiments.
Figures 7A, 7B, 7C:
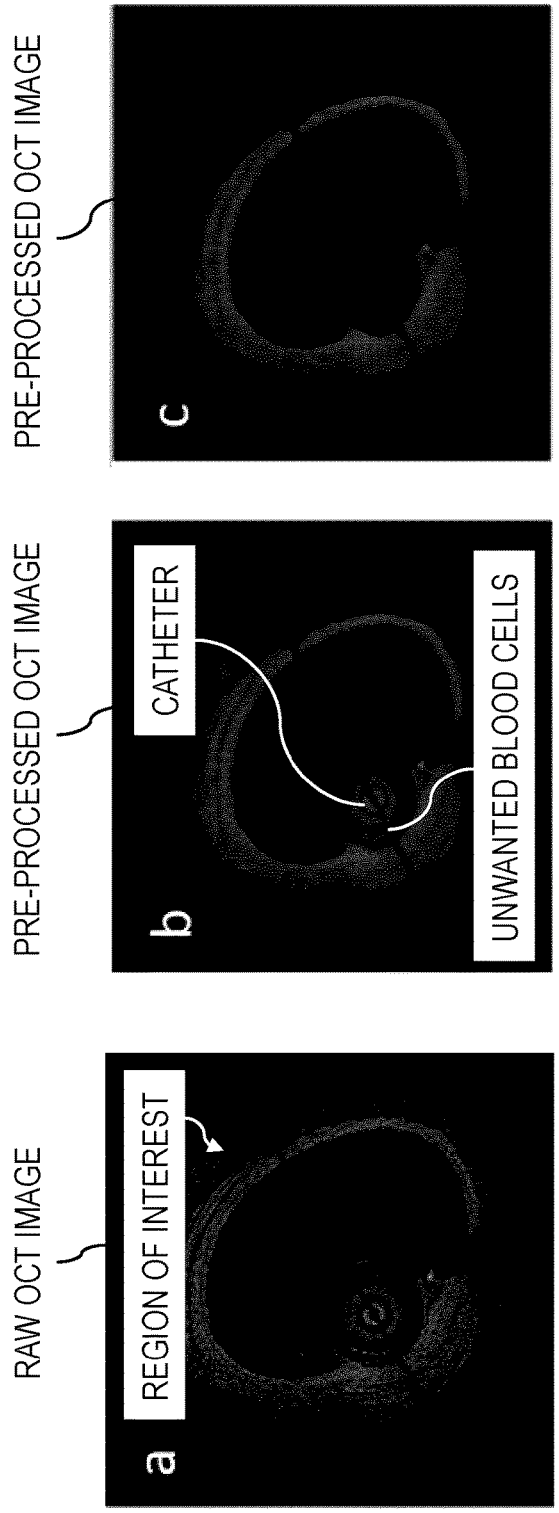
FIG. 7A is an example of a raw OCT image, in accordance with one or more embodiments.
FIG. 7B is an example of an OCT image which has been pre-processed to detect a detect a region of interest therein using active contour, in accordance with one or more embodiments.
FIG. 7C is an example of an OCT image which has been pre-processed to remove a catheter and unwanted blood cells, in accordance with one or more embodiments.

Referring now to FIG. 6, in some embodiments, the system 100 may be accessible remotely from any one of a plurality of external devices 630 over connections 628. External devices 630 may be any one of a desktop, a laptop, a tablet, a smartphone, and the like. External devices 630 may have a software application such as software application 300 of FIG. 3 provided wholly or partly thereon as a downloaded software application, a firmware application, or a combination thereof, for accessing the system 100 of FIG. 1. Alternatively, external devices 630 may access the system 100 of FIG. 1 via a web application, accessible through any type of Web browser.

The connections 628 may comprise wire-based technology, such as electrical wires or cables, and/or optical fibers. The connections 628 may also be wireless, such as RF, infrared, Wi-Fi, Bluetooth, and others. The connections 628 may therefore comprise a network, such as the Internet, the Public Switch Telephone Network (PSTN), a cellular network, or others known to those skilled in the art. Communication over the network may occur using any known communication protocols that enable external devices 630 within a computer network to exchange information. The examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol).

In some embodiments, the software application 300 of FIG. 3 is provided at least in part on any one of external devices 630. For example, the software application 300 may be configured as a first portion provided in the system 100 of FIG. 1 to obtain and transmit the inputs such as the feature vectors to a second portion, provided on one of the external devices 630. The second portion may be configured to receive the inputs such as the OCT image 104 and/or the feature vectors 308, and perform the steps carried by the classification engines 306 on one of the external devices 630. Alternatively, the software application 300 is provided entirely on any one of the external devices 630 and is configured to receive an OCT image 104 from a remote OCT imaging system. Also alternatively, the system 100 of FIG. 1 can be configured to transmit, via connections 628, one or more of inputs such as the OCT image 104, the feature vectors 308, the preliminary coronal artery tissue types 310 and/or the output coronal artery tissue types 116. Other embodiments may also apply.

One or more databases 632, such as databases 634A, 634B and/or 634C may be provided locally on any one of the system 100 of FIG. 1 and the external devices 630, or may be provided separately therefrom (as illustrated). In the case of a remote access to the databases 632, access may occur via the connections 628 taking the form of any type of network, as indicated above. The various databases 632 described herein may be provided as collections of data or information organized for rapid search and retrieval by a computer. The databases 632 may be structured to facilitate storage, retrieval, modification, and deletion of data in conjunction with various data-processing operations. The databases 632 may be any organization of data on a data storage medium, such as one or more servers. The databases 632 illustratively have stored therein raw data representing training OCT images 524 and associated truth tissue type 526 and truth abnormality.

Each software application described herein may be implemented in a high level procedural or object-oriented programming or scripting language, or a combination thereof, to communicate with a computer system. Alternatively, the software applications may be implemented in assembly or machine language. The language may be a compiled or interpreted language. Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Example 1—Deep Characterization of Coronary Artery Tissue Layers from OCT Imaging Kawasaki Disease (KD), mucocutaneous lymph node syndrome, is an acute childhood vasculitis syndrome, which is the leading cause of coronary artery sequelae, complicated by coronary artery aneurysms with subsequent intimal hyperplasia, disappearance of media, neovascularization, fibrosis, calcification, and macrophage accumulation. In normal three-layered structure of coronary artery using OCT imaging, intima is characterized as a signal rich well-delineated layer and media appears as a homogeneous signal poor pattern specified by the internal and external elastic lamina. The outermost layer is adventicia, which is characterized as a signal rich layer. Intimal hyperplasia is the most frequent complication caused by KD, which is thickening of the intima and can be followed by media destruction, since media becomes thinner and finally disappear as a result of plaque accumulation and vessel remodeling. Intimal thickening can disturb oxygen diffusion and cause proliferation of vasa vasorum in inner layers of arterial wall, which is called neovascularization. Presence of neovascularization may be a sign of plaque instability and rupture and is characterized in OCT images as signal poor voids. Fibrosis is scarring of the connective tissues, which may occur as a result of arterial inflammation and is characterized as signal rich areas in OCT imaging. Macrophage may be accumulated within a fibrous cap as a result of monocytes differentiation in confronting with arterial wall inflammation. Macrophage is visualized as a confluent signal rich focal area in OCT imaging. Vascular smooth muscle cells (VSMCs) regulate mineralization in intima and media. Rising lipid content within arterial lesions and inflammatory mediators may transform vascular smooth muscle cells to an osteoblast phenotype, resulting in intimal calcification. Calcification may be extended within a fibrous cap, which is visualized as a signal poor area with sharply delineated borders in OCT imaging.

Cardiovascular Optical Coherence Tomography (OCT) is a catheter-based invasive imaging modality, which typically employs a near-infrared light to provide cross-sectional images of coronary artery at depth of several millimeters relying on low-coherence interferometry. The unique characteristic of OCT is its high axial resolution of 10-15 µm, which is measured by the light wavelength and is decoupled from the lens dependent lateral resolution ranging from 20-40 µm. The image-wire is inserted into the coronary artery using an over-the-wire balloon catheter from patient's groin. A sequence of cross-sectional images of coronary artery segment is recorded using the backscattered light from the arterial wall through each pullback. Considering the fact that light can be attenuated by blood before reaching the vessel wall, blood clearance is required before starting the image acquisition.

Progression of pathological formations caused by coronary artery disease can be followed by acute coronary syndrome (ACS). Therefore, it is significant to develop robust coronary artery tissue characterization techniques to evaluate pathological formations. While conventional imaging techniques such as CT and MRI may be used for clinical assessment of the coronary arteries, they are limited in providing useful information about the underlying coronary artery tissue layers. Also, they are restricted to reflect the histological reality of the regressed aneurysmal coronary segments, which are inappropriately considered as normal coronary segments. Catheter based Intravascular Ultrasound (IVUS) has been used for many years in interventional cardiology to evaluate coronary artery tissues by providing information on coronary arterial wall and lumen. IVUS imaging is restricted to be used in pediatric cardiology due to its suboptimal spatial imaging resolution (100-150 µm), and low pullback speed. Arterial plaque formations are structural abnormalities, which require a high resolution imaging modality to be detected.

Automated tissue analysis and plaque detection were focused on 2D intracoronary OCT images in adult patients to visualize plaque formations. Combination of light backscattering, and attenuation coefficients have been estimated from intracoronary time domain OCT for three different atherosclerosis tissues, namely calcification, lipid pool, and fibrosis. Characterizing fibrosis and calcification in coronary atherosclerosis was generally performed by estimating the optical attenuation coefficient. The estimated values were compared with histopathological features of each tissue to determine the corresponding optical properties. Another reference proposed a tissue classification method using support vector machine (SVM) with the combination of texture features and optical attenuation coefficient extracted form atherosclerotic tissues. Volumetric estimation of backscattered intensity, and attenuation coefficient has been published. Classification approach using SVM was used to discriminate between fibrosis, calcification, and lipid. Identification and quantification of fibrous tissue based on Short-Time Fourier Transform (STFT) using OCT imaging was proposed. A classification framework to detect normal myocardium, loose collagen, adipose tissue, fibrotic myocardium, and dense collagen has been developed. Graph searching method is applied to segment various tissue layers of coronary artery. Combination of texture features, and optical properties of tissues is used to train a relevance vector machine (RVM) to perform the classification task. A plaque tissue characterization technique based on intrinsic morphological characteristics of the A-lines using OCT imaging has been proposed. to classify superficial-lipid, fibrotic-lipid, fibrosis, and intimal thickening by applying Linear Discriminant Analysis (LDA).

Convolutional Neural Networks (CNNs) have gained a wide popularity in medical image analysis. Application of CNNs in medical image analysis was first demonstrated for lung nodule detection. This idea was extended to various applications in the field of medical imaging. More recently, CNNs have been introduced in coronary OCT imaging to classify tissue layers between media and intima using SVM and Random Forest classifiers.

Transferability is defined as transferring the knowledge embedded in the pre-trained CNNs for other applications, which is performed in two different ways: Using a pre-trained network as feature generator, and fine-tuning a pre-trained network to be used for classification of medical images. Common networks, which are used as pre-trained models with applications in medical image analysis are categorized in three groups. Simple networks with few convolutional layers use kenels with large receptive fields in upper layers close to the input and smaller kernels in deeper layers. The popular network in this group, which has a broad application is medical image analysis is AlexNet. The second group of architectures are deep networks such as Vgg models. They have the same configuration as simple networks with more convolutional layers and kernels with smaller receptive fields. The third group of networks are categorized as complex building blocks with higher efficiency of the training process compared against other group of networks. GoogleNet was the first network in this categor. ResNet and Inception models are other networks of this group. An improved version of GoogleNet, which is used recently in the field of medical image analysis is Inception-v3. Vgg-16, VGG-M-128, and BVLC reference CaffeNet are used as feature extractors to classify the knee osteoarthritis (OA) images by training SVM using deep features. Pre-trained networks were also used for the application of cytopathology classification. It is demonstrated in their work that using a pre-trained network as feature extractor outperforms the fine-tuning of the network. Inception-v3 model has been fine-tuned to classify skin lesions. The fine-tuned network has been used to evaluate the retinal fundus photographs from adults by detecting referable diabetic retinopathy. In these studies, it is demonstrated that the results of classification using fine-tuned network competes against the human expert performance. Nevertheless, most of the studies are focused on fine-tuning the networks and comparison of the results of fine-tuned networks with the results of other classifiers, which are trained on deep features.

This example focuses on designing a tissue characterization model to detect pathological formations in coronary artery tissues using OCT imaging. To find the optimal model to classify calcification, fibrosis, neovascularization, macrophage, and coronary artery layers, intima and media, four different experiments were performed. Then, the optimal model is chosen by applying three different pre-trained networks as feature extractors. Random Forest is trained on each set of deep features separately to perform classification. classification results of Random Forest using three various set of deep features are combined using majority voting approach to provide the final classification result. Hence, the contributions of this example are: i) characterization of complex pathological formations in KD from OCT imaging, namely intimal hyperplasia, disappearance of media, neovascularization, fibrosis, calcification, and macrophage accumulation; ii) evaluation of different pre-trained CNN models for OCT image analysis with a limited labeled dataset; and iii) assessment of the clinical usefulness of deep feature learning for OCT imaging in pediatric cardiology.

The experiments are performed on 33 pullbacks of intracoronary cross-sectional OCT images of patients affected by KD. The images are acquired using the ILUMIEN OCT system (St. Jude Medical Inc., St. Paul, Minnesota, USA) with the axial and lateral resolutions of 12-15 µm and 20-40 µm respectively. Image acquisition is performed using FD-OCT with pullback speed of 20 mm/sec and frame rate of 100 frames/sec. For the first step, the pre-processing is performed on all the frames of each sequence by automatic recognition and removal of the guide-wire. Then, the approximate region of interests including the lumen, intima, media, calcification, neovascularization, macrophage, fibrosis and surrounding tissues are detected for each pullback frame using active contour. Catheter and unwanted blood cells are removed by applying the smallest connected components approach (See FIGS. 7A-C). The images were converted to planar by transferring all the points from Cartesian coordinates to planar representation in Polar coordinates to simplify the calculations.

CNNs are built on convolutional layers, which are responsible to extract features from local receptive field of the input image. Each convolutional layer consists of n sets of shared weights between the nodes to find similar local features in the input channels, which are called convolutional kernels. Each kernel creates a feature map when it slides through the whole input image with a defined stride. Feature maps extracted form one convolutional layer will be the input of the next layer. It is standard to calculate the output of a neuron by applying a hyperbolic tangent or logistic regression, which are both saturating activation functions. Saturating nonlinearities are slower than non-saturating nonlinearities while stochastic gradient descent is used to minimize the cost function with respect to the weights at each convolutional layer. Therefore, a non-saturating activation function, which is called Rectified Linear Unit (ReLU) can accelerate the training process by keeping non-negative values and replacing negative values by zero in the feature map. ReLU is defined as follows:

$$f(x) = \max(0, x) \quad (1)$$

Where f is the output of each neuron as a function of its input x. CNNs alternate between the convolutional and pooling layers to achieve computational efficiency, since pooling layers are used for dimensionality reduction by aggregating the outputs of neurons at one convolutional layer and reducing the size of the feature maps. Pooling layers can keep the network invariant to small transformations, distortions, and translations in the input image as well as controlling overfitting by reducing the number of parameters and computations. Max pooling is used in most of the CNN architectures, which choose the superior invariant features in specified neighborhoods of a feature map.

CNNs are trained using back-propagation algorithm and stochastic gradient descent is commonly used to minimize the following cost function:

$$L = -(1/|X|)\Sigma_j^{|x|} \ln(p(y^j|Xj)) \quad (2)$$

Where X is the size of the training set and $\ln(p(y^j|Xj))$ denotes the probability of $j^{th}$ image to be classified correctly with the corresponding label y. for each layer of the network, the weights are updated at each iteration i as follows:

$$V_{i+1} = \mu V_i - y_i \alpha \partial L / \partial W \quad (3)$$

$$W_{i+1} = W_i + V_{i+1} \quad (4)$$

Where µ is the momentum, a is the learning rate, y is the scheduling rate, which reduces the learning rate at the end of iterations, and W is the weight at each iteration i for each layer.

Pre-trained networks are widely used as both feature extractor and classifier for different tasks. Among the most common architectures, three pre-trained networks with different architectures were selected. AlexNet is a simple and shallow network, which is popular for clinical applications. The network consists of five convolutional layers, and three fully connected layers, which are followed by a final softmax with GPU implementation of convolutional operation. The model is trained on 1.2 million images from the ImageNet dataset, which are annotated and categorized into 1000 semantic classes. The model uses 60 million parameters and consists of 650000 neurons, which is trained using stochastic gradient descent with the batch size of 128, momentum of 0.9, and weight decay of 0.0005 to reduce the training error of the model. Examples of the AlexNet simple architecture network are discussed in i) A. Krizhevsky, I. Sutskever, and G. E. Hinton, "Imagenet classification with deep convolutional neural networks," in Advances in Neural Information Processing Systems, (2012), pp. 1097-1105 and ii) G. Litjens, T. Kooi, B. E. Bejnordi, A. A. A. Setio, F. Ciompi, M. Ghafoorian, J. A. van der Laak, B. van Ginneken, and C. I. Sanchez, "A survey on deep learning in medical image analysis," Med. Image Analysis 42, 60-88 (2017), the entire contents of which are hereby incorporated by reference.

TABLE 1

Detail of the AlexNet simple architecture network.

| Layer | Layer Type | Input of Each Layer | Output |
|---|---|---|---|
| conv1 | Convolution | 227 × 227 × 3, stride [4 4], padding [0 0] | 55 × 55 × 96 |
| pool1 | Max pooling | 55 × 55 × 96, stride [2 2], padding [0 0] | 27 × 27 × 96 |
| conv2 | Convolution | 27 × 27 × 96, stride [1 1], padding [2 2] | 27 × 27 × 256 |
| pool2 | Max pooling | 27 × 27 × 256, stride [2 2], padding [0 0] | 13 × 13 × 256 |
| conv3 | Convolution | 13 × 13 × 256, stride [1 1], padding [1 1] | 13 × 13 × 384 |
| conv4 | Convolution | 13 × 13 × 384, stride [1 1], padding [1 1] | 13 × 13 × 384 |
| conv5 | Convolution | 13 × 13 × 384, stride [1 1], padding [1 1] | 13 × 13 × 256 |
| pooling5 | Max pooling | 13 × 13 × 256, stride [2 2], padding [0 0] | 6 × 6 × 256 |

TABLE 1-continued

Detail of the AlexNet simple architecture network.

| Layer | Layer Type | Input of Each Layer | Output |
|---|---|---|---|
| fc6 | Fully connected | 6 × 6 × 256 | 1 × 4096 feature vector |
| fc7 | Fully connected | 1 × 4096 feature vector | 1 × 4096 feature vector |
| fc8 | Fully connected | 1 × 4096 feature vector | 1 × 1000 |

Deeper models were designed by stacking convolutional layers to increase the depth of the network. Instead of using a large receptive field, kernels with very small receptive field and fixed size were applied in each convolutional layer. Every set of convolutional layers is followed by a max pooling to reduce dimensionality, and every convolutional layer is followed by a ReLU to introduce non-linearity. Vgg networks are trained on 1.2 million of images of 1000 classes from ImageNet. The batch size and momentum are set to 256, and 0.9 respectively. The learning rate was initialized to 0.01 and was decreased by factor of 10 when the accuracy on validation set stopped improving. Among deep network architectures of Vgg, Vgg-19 was selected with 144 million of parameters and deeper network architecture consists of 16 convolutional layers, and three fully connected layers. Examples of the Vgg-19 deep architecture network are discussed in i) K. Simonyan and A. Zisserman, "Very deep convolutional networks for large-scale image recognition," arXiv preprint arXiv:1409.1556 (2014) and ii) G. Litjens, T. Kooi, B. E. Bejnordi, A. A. A. Setio, F. Ciompi, M. Ghafoorian, J. A. van der Laak, B. van Ginneken, and C. I. Sanchez, "A survey on deep learning in medical image analysis," Med. Image Analysis 42, 60-88 (2017), the entire contents of which are hereby incorporated by reference.

TABLE 2

Detail of the Vgg-19 deep architecture network.

| Layer | Layer Type | Input of Each Layer | Output |
|---|---|---|---|
| conv1_1 conv1_2 | Convolution | 224 × 224 × 3, 64 filters 3 × 3, stride 1, padding 1 | 224 × 224 × 64 |
| pool1 | Max pooling | 2 × 2, stride 2, padding 0 | |
| conv2_1 conv2_2 | Convolution | 128 filters 3 × 3, stride 1, padding 1 | 112 × 112 × 128 |
| pool2 | Max pooling | 2 × 2, stride 2, padding 0 | |
| conv3_1 conv3_2 conv3_3 conv4_4 | Convolution | 256 filters 3 × 3, stride 1, padding 1 | 56 × 56 × 256 |
| pool3 | Max pooling | 2 × 2, stride 2, padding 0 | |
| conv4_1 conv4_2 conv4_3 conv4_4 | Convolution | 512 filters 3 × 3, stride 1, padding 1 | 28 × 28 × 512 |
| pool4 | Max pooling | 2 × 2, stride 2, padding 0 | |
| conv5_1 conv5_2 conv5_3 conv5_4 | Convolution | 512 filters 3 × 3, stride 1, padding 1 | 14 × 14 × 512 |
| pool5 | Max pooling | 2 × 2, stride 2, padding 0 | |
| fc6 | Fully connected | 6 × 6 × 256 | 1 × 4096 feature vector |
| fc7 | Fully connected | 1 × 4096 feature vector | 1 × 4096 feature vector |
| fc8 | Fully connected | 1 × 4096 feature vector | 1 × 1000 |

Complex building blocks (inception blocks) are introduced as models with fewer number of parameters and higher efficiency of the training process by replacing the fully connected building blocks called inception modules, which are stacked on top of each other. Each inception module consists of combination of convolutional layers with kernel sizes of 1×1, 3×3, and 5×5, which their output filter banks concatenated into a single output vector that will be the input of the next stage. 1×1 convolutions in each inception module is used for dimensionality reduction before applying computationally expensive 3×3 and 5×5 convolutions. Factorization of convolutions into smaller convolutions results in aggressive dimension reduction inside the network, which leads to fewer number of parameters and low computational cost. Inception models are trained using stochastic gradient descent. Batch size is chosen as 32 for 100 epochs and momentum with the decay of 0.9. Learning rate is initialized by 0.045 and decayed every second epoch by the exponential rate of 0.94. Pre-trained Inception-v3 is used in the experiments presented herein. The inception models are updated in this version of network to further boost ImageNet classification accuracy. Examples of the Inception-v3 complex architecture network are discussed in i) G. Litjens, T. Kooi, B. E. Bejnordi, A. A. A. Setio, F. Ciompi, M. Ghafoorian, J. A. van der Laak, B. van Ginneken, and C. I. Sanchez, "A survey on deep learning in medical image analysis," Med. Image Analysis 42, 60-88 (2017). ii) C. Szegedy, V. Vanhoucke, S. loffe, J. Shlens, and Z. Wojna, "Rethinking the inception architecture for computer vision," in Proceedings of the IEEE Conference on Computer Vision and Pattern Recognition, (2016), pp. 2818-2826, and iii) C. Szegedy, W. Liu, Y. Jia, P. Sermanet, S. Reed, and D. Anguelov, "Going deeper with convolutions," in Proceedings of the IEEE conference on Computer Vision and Pattern Recognition, pp. 1-9, the entire contents of which are hereby incorporated by reference.

In these experiments, the total of ~5100 different tissues are extracted from OCT pullback images and are manually labeled as calcification, fibrosis, intima, macrophage, media, and neovascularization. To start the experiments, 66% of the ROIs are selected randomly as training set. To avoid any correlation between training, test, and validation sets, 50% of the remaining ROIs are randomly selected as the validation set and test set is built on the last residual ROIs. The experiments are performed in four different steps to find the optimal tissue characterization framework.

For each convolutional neural network, before starting the training process, the iterative weight update is performed by random weight initialization at each layer of the network. Since the number of labeled data is limited in the experiments presented herein, weight initialization can be performed using the weights of the pre-trained networks. Therefore, iterative weight updates of equations 5.3 and 5.4 lead to a fast convergence to find the desirable local minimum for the cost function (equation 5.2). Considering the fact that number of nodes in the last fully connected layer depends on the number of classes in each dataset, the first step before starting the fine-tuning is to keep the same architecture as the pre-trained network architecture, remove the classification layers and replace them by the layers, which are designed appropriately for the classification task. The next step is to initialize the weights at each layer of the network with the weights of pre-trained network, which is called transfer learning. the iterative weight update can be started using layer-wise fine-tuning by finding the optimal learning parameters at each convolutional and fully connected layer. Fine-tuning AlexNet for classification of coronary artery layers (intima and media) was preformed. Since, a goal of this example is to develop a tissue characterization model to detect pathological formations (calcification, fibrosis, macrophage, and neovascularization) as well as the arterial wall layers, the process of fine-tuning the pre-trained AlexNet is improved based on the dataset. the last three layers of the pre-trained network (fc8, prob, and classification layer) are replaced by a set of layers which are designed for multi-class classification task to classify calcification, fibrosis, macrophage, neovascularization, intima, and media. The depth of fine-tuning is increased compared against previous work, since AlexNet is not a very deep model, low-level features extracted from the first convolutional layers can improve the classification precision while various tissue labels are dealt with to preform the classification task. The values of p and y are kept at 0.9 and 0.95 respectively and the learning rate for the last fully connected layers (fc6, fc7, and fc8) is set to 0.1 to learn faster in the last layers. The learning rates were decreased to 0.01 from the last convolutional layer (Conv3).

Since by adding convolutional layers with corresponding kernels, access is granted to detailed image information, increasing the depth and width of the network can improve the quality of the network architecture. To have a fair comparison among performance of pre-trained networks, Vgg-19 was selected from the category of very deep CNN architectures. As it is explained in the previous section, Vgg-19 has almost the same configuration of the AlexNet with more convolutional layers. Therefore, fine-tuning the Vgg-19 is performed using the same strategy that is applied on AlexNet. Fine-tuning was started by removing the classification layers (fc8, prob, and output) and replaced them by a set of layers, which are appropriate for multi-class classification of various coronary artery tissues (calcification, fibrosis, macrophage, neovascularization, intima, and media). Fine-tuning was started from the last fully connected layer (fc8) and increase the depth of fine-tuning gradually by evaluating the network performance at each fine-tuning level. To find the optimal parameters at each level of fine-tuning, an interval of values close to the optimal values of fine-tuned AlexNet is chosen. Then the optimal parameters are determined by grid searching for defined interval of values and evaluating the performance of the network at each step. The best performance of the network obtained by assigning fixed values of 0.8, and 0.85 to p and respectively. The learning rate is determined as 0.2 for the last fully connected layers (fc6, fc7, and fc8) and is decreased to 0.01 from the last convolutional layer (Conv5-4).

complex building blocks are very deep network architectures, which uses the particular configuration of inception modules to reduce the number of parameters and consequently improve the efficiency of the training procedure. Inception-v3 was selected from the category of complex network architectures to perform the experiments. Considering the complexity of the Inception architectures, changing the network can interfere computational gains. Therefore, it is more difficult to adapt these types of networks to a classification task. To fine-tune the network, the last layers of the network (predictions, predictions-softmax, and Classification-Layer-predictions) were removed, which aggregating the extracted features from the network for classification task and added a set of classification layers adapted to the data set to the network graph. The layers are connected to the transferred network graph and the learning rate for the fully connected layer is set to 0.1.

At each step of fine-tuning for all networks, the accuracy is calculated on the validation set and the training process is stopped when the highest accuracy on the validation set is obtained. By terminating the training process, classification is performed on test set using each fine-tuned network separately.

Figure 8:
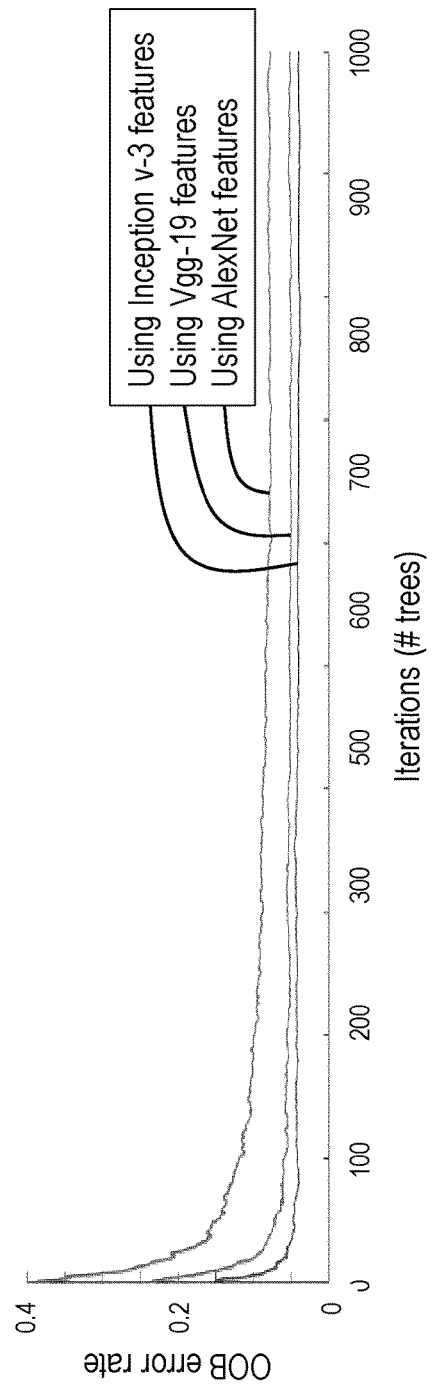
FIG. 8 is a graph showing out-of-bag (OOB) error rate as function of iterations during training of a classification engine using feature vectors from different feature extraction engines, in accordance with one or more embodiments.
Figures 9A, 9B, 9C:
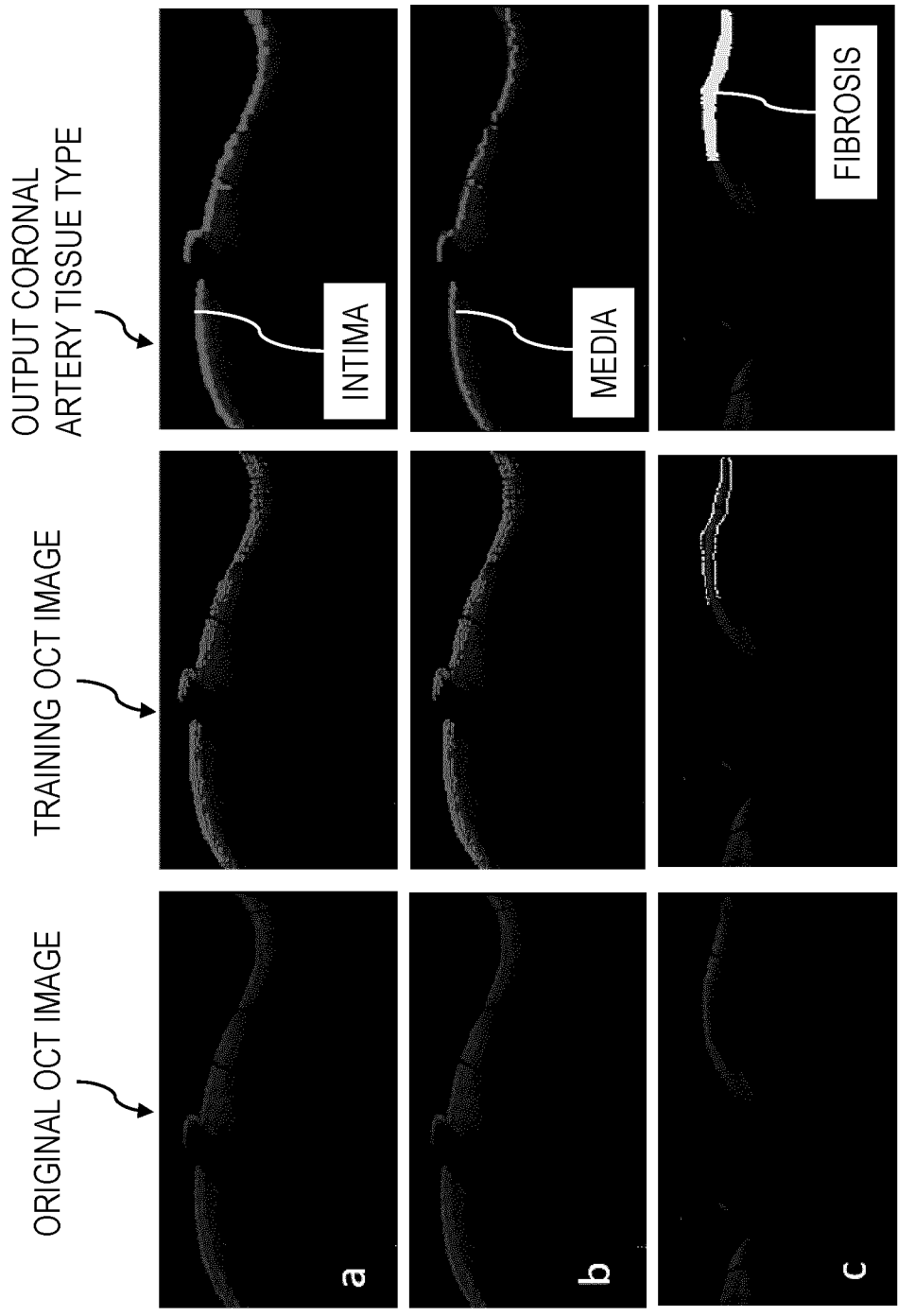

In this experiment, pre-trained networks are used as feature generators. The activations extracted from the last layer before classification layer is used to train Random Forest to classify various coronary artery tissues. Using AlexNet, and Vgg-19, features are extracted from the last fully connected layer right before the classification layer (fc7). Each feature vector represents 4096 attributes of the labeled tissue. Using Inception-v3, features are extracted from the last depth concatenation layer (mixed10). Each feature vector represents 131072 attributes of the labeled tissue. It is demonstrated that Random Forest is a robust classifier with quick training process and low risk of overfitting. It works based on generating an ensemble of trees. The trees are grown based on the CART methodology to maximum size without pruning. Generalization error for Random Forest classifier is proportional to the ratio $p/s^2$, which (s) and (p) are respectively defined as the strength of the trees and correlation between them. the smaller this ratio results in the better performance of Random Forest. To find the optimal number of trees, The performance of Random Forest is evaluated for 1000 of trees while it is trained on each set of features extracted from each network separately. The OOB error rate is stopped decreasing when the tree number is assigned to 250 using the features extracted from Inception-v3, and Vgg-19, and 300 using the features extracted from AlexNet (see FIG. 8). Fewer number of trees accelerates the training process by reducing the computational complexity. The number of randomly selected predictors is set to 7.

Training features extracted from each pre-trained network and used separately to train Random Forest. Classification is performed on test set using the test features extracted by each pre-trained network.

Inspired by the ensemble learning approaches, weighted majority voting was applied on the classification results obtained by the second experiment. Classification is performed by Random Forest using the features extracted from AlexNet, Vgg-19, and Inception-v3. Using the following equation, for weighted majority voting, weights are set to ⅓ for all the three sets of classification results except those labels with three different tissue labels.

$$C(x) = \operatorname{argmax}_i \sum_j w_j I(C_j(x) = i) \tag{5}$$

Where C(x) is the classification label with majority vote, i is the class label (it can be varying from 1 to 6 for calcification, fibrosis, intima, macrophage, media, and neovascularization), $w_j$ is the weight of $j^{th}$ tissue label, and I is the indicator function. Thus, majority voting is applied to search in all the classification labels for the most frequent label assigned to each tissue using equation (6).

$$C(x) = \text{mode}\{C_1(x), C_2(x), C_3(x)\} \quad (6)$$

Where $C_1(x)$, $C_2(x)$, and $C_3(x)$ are Random Forest classification results using the features extracted from AlexNet, Vgg-19, and Inception-v3 respectively. Since the mode of $C_1(x)$, $C_2(x)$, and $C_3(x)$ when $C_1(x) \neq C_2(x) \neq C_3(x)$ gives us the smallest tissue label as the majority vote, more weight is put on the third group of predicted labels if $C_1(x) \neq C_2(x) \neq C_3(x)$ considering the strength of deep Inception-v3 features. Therefore, the majority vote will be on the class label with highest probability of belonging to the true class label.

To consider all possible ways to find the optimal tissue characterization framework, the features obtained from AlexNet, and Vgg-19 were combined to train Random Forest. Classification is performed on test set and the results are compared against the previous experiments. The features extracted from Inception-v3 is not used in this experiment since the size of the feature matrix is huge to be combined with other feature matrices.

For each experiment, the classification is performed to characterize six different coronary artery tissues (calcification, fibrosis, macrophage, neovascularization, intima, and media). The results obtained for each experiment as follows.

For the first experiment, fine-tuning is performed on AlexNet, Vgg-19, and Inception-v3 from different categories of simple architectures, very deep architectures, and complex networks respectively. The optimal fine-tuning parameters are estimated and the networks are trained by assigning learning parameters. Classification is performed by each network separately and accuracy, sensitivity, and specificity are measured using the corresponding confusion matrix for each network. The results are shown and Tables 3-5.

TABLE 3

Measured sensitivity, specificity, and accuracy of tissue classification using fine-tuned AlexNet.

| Tissue | Accuracy | Sensitivity | Specificity |
|---|---|---|---|
| Calcification | 0.95 | 0.92 | 0.99 |
| Fibrosis | 0.92 | 0.85 | 0.99 |
| Intima | 1.00 | 1.00 | 1.00 |
| Macrophage | 0.89 | 0.82 | 0.97 |
| Media | 1.00 | 0.99 | 1.00 |
| Neovascularization | 0.98 | 1.00 | 0.97 |

TABLE 4

Measured sensitivity, specificty, and accuracy of tissue classification using fine-tuned Vgg-19.

| Tissue | Accuracy | Sensitivity | Specificity |
|---|---|---|---|
| Calcification | 0.95 | 0.92 | 0.99 |
| Fibrosis | 1.00 | 1.00 | 1.00 |
| Intima | 1.00 | 1.00 | 1.00 |
| Macrophage | 0.95 | 0.91 | 1.00 |
| Media | 1.00 | 1.00 | 1.00 |
| Neovascularization | 0.99 | 1.00 | 0.99 |

TABLE 5

Measured sensitivity, specificity, and accuracy of tissue classification using fine-tuned Inception-v3.

| Tissue | Accuracy | Sensitivity | Specificity |
|---|---|---|---|
| Calcification | 1.00 | 1.00 | 1.00 |
| Fibrosis | 0.96 | 0.92 | 0.99 |
| Intima | 1.00 | 1.00 | 1.00 |
| Macrophage | 0.95 | 0.91 | 0.99 |
| Media | 1.00 | 1.00 | 1.00 |
| Neovascularization | 0.97 | 0.95 | 1.00 |

The results of the experiments demonstrate the higher performance of Vgg-19 and Inception-v3 compared against AlexNet, which was expected considering the deep structure of Vgg-19, and Inception-v3 architectures. Although using pre-trained networks reduce the computational burden, which results in reducing the training time and convergence issues, but considerable amount of time is still required to find the optimal learning parameters and retrain the fine-tuned networks (approximately two hours for each network). Also, there is a risk of overfitting in deep fine-tuning a network. The following steps are proposed to find the optimal tissue characterization model, which can overcome the mentioned issues in an efficient way.

In this experiment, deep features are extracted from AlexNet, Vgg-19, and Inception-v3. By applying each network separately as feature generator, the training features are extracted to train Random Forest and the classification is performed on test set. Features are extracted from the last fully connected layer before the classification layer (fc7) in AlexNet, and Vgg-19 architectures, and the last depth concatenation layer (mixed10) in Inception-v3 architecture. Accuracy, sensitivity, and specificity are measured using the corresponding confusion matrix for each classification result, which are shown in Tables 6-8.

TABLE 6

Measured sensitivity, specificity, and accuracy of tissue classification using RF. Features are extracted from AlexNet.

| Tissue | Accuracy | Sensitivity | Specificity |
|---|---|---|---|
| Calcification | 0.95 | 0.92 | 0.98 |
| Fibrosis | 0.95 | 0.92 | 0.99 |
| Intima | 0.99 | 1.00 | 1.00 |
| Macrophage | 0.80 | 0.64 | 0.95 |
| Media | 0.99 | 1.97 | 1.00 |
| Neovascularization | 0.92 | 1.89 | 0.95 |

TABLE 7

Measured sensitivity, specificity, and accuracy of tissue classification using RF. Features are extracted from Vgg-19.

| Tissue | Accuracy | Sensitivity | Specificity |
|---|---|---|---|
| Calcification | 1.00 | 1.00 | 1.00 |
| Fibrosis | 0.92 | 0.85 | 0.99 |
| Intima | 0.98 | 0.97 | 0.99 |
| Macrophage | 0.91 | 0.82 | 1.00 |
| Media | 0.98 | 0.97 | 0.98 |
| Neovascularization | 0.97 | 0.95 | 1.00 |

TABLE 8

Measured sensitivity, specificity, and accuracy of tissue classification using RF. Features are extracted from Inception-v3.

| Tissue | Accuracy | Sensitivity | Specificity |
|---|---|---|---|
| Calcification | 0.90 | 0.83 | 0.97 |
| Fibrosis | 0.95 | 0.92 | 0.99 |
| Intima | 0.95 | 0.91 | 0.98 |
| Macrophage | 0.90 | 0.82 | 0.99 |
| Media | 0.96 | 0.94 | 0.98 |
| Neovascularization | 0.96 | 0.95 | 0.97 |

Regardless of the time, which is spent to find the optimal learning parameters, the process of feature extraction from all the three networks, and training the Random Forest using each set of features takes approximately twice less time than retraining a network. Using pre-trained networks as feature extractor overcomes the problems of fine-tuning, training time, and overfitting concerns. But, the classification performance is not as high as using CNNs as classifiers. To solve this problem, the following two experiments are performed and the results of all experiments compared against each other.

In this experiment, weighted majority voting is applied on Random Forest classification results using each set of features extracted from the three mentioned networks. The results are illustrated in Table 9. The results show a good improvement of accuracy, sensitivity, and specificity, which are calculated for the final classification using majority voting.

TABLE 9

Measured sensitivity, specificity, and accuracy of tissue classification using majority voting approach.

| Tissue | Accuracy | Sensitivity | Specificity |
|---|---|---|---|
| Calcification | 1.00 | 1.00 | 1.00 |
| Fibrosis | 1.00 | 1.00 | 1.00 |
| Intima | 0.99 | 0.98 | 1.00 |
| Macrophage | 0.95 | 0.91 | 1.00 |
| Media | 0.99 | 0.99 | 1.00 |
| Neovascularization | 1.00 | 1.00 | 1.00 |

In this example, deep features extracted from AlexNet, and Vgg-19 are combined to train Random Forest. The results are shown in Table 10. The results of the last two experiments show that majority voting approach performs better than Random Forest classification result while it is trained on combination of features.

TABLE 810

Measured sensitivity, specificity, and accuracy of tissue classification: Combination of features extracted from pre-trained AlexNet, and Vgg-19 are used to train Random Forest.

| Tissue | Accuracy | Sensitivity | Specificity |
|---|---|---|---|
| Calcification | 1.00 | 1.00 | 1.00 |
| Fibrosis | 0.96 | 0.92 | 1.00 |
| Intima | 1.00 | 1.00 | 1.00 |
| Macrophage | 0.90 | 0.82 | 0.98 |
| Media | 0.99 | 0.99 | 1.00 |
| Neovascularization | 0.91 | 0.84 | 0.98 |

To choose the optimal tissue characterization model considering all the experiments, and to compare the results of the experiments against each other, the mean±standard deviation of the values of accuracy, sensitivity, and specificity obtained for all tissues performing each experiment are calculated and the results are shown in Table 11. Although combination of features can improve the classification results compared against using each network separately as feature extractor, but the results of majority voting approach are considerably higher than the classification results using combination of features.

TABLE 11

Accuracy, sensitivity, and specificity obtained from each experiment. The accuracy, sensitivity, and specificity are reported as the mean ± standard deviation of the values of accuracy, sensitivity, and specificity obtained for all tissues performing each experiment.

| Tissue | Accuracy | Sensitivity | Specificity |
|---|---|---|---|
| Fine-tuned AlexNet | 0.96 ± 0.04 | 0.93 ± 0.07 | 0.99 ± 0.01 |
| Fine-tuned Vgg-19 | 0.98 ± 0.02 | 0.97 ± 0.03 | 1.00 ± 0.00 |
| Fine-tuned Inception-v3 | 0.98 ± 0.02 | 0.96 ± 0.04 | 1.00 ± 0.00 |
| RF(AlexNet features) | 0.93 ± 0.07 | 0.89 ± 0.11 | 0.98 ± 0.02 |
| RF(VGG-19 features) | 0.96 ± 0.04 | 0.92 ± 0.07 | 0.99 ± 0.01 |
| RF(Inception-v3 features) | 0.94 ± 0.03 | 0.90 ± 0.06 | 0.98 ± 0.01 |
| Majority voting RF | 0.99 ± 0.01 | 0.98 ± 0.04 | 1.00 ± 0.00 |
| RF(combination of features) | 0.94 ± 0.06 | 0.90 ± 0.10 | 0.99 ± 0.01 |

In this example, the performance of pre-trained networks is discussed. Three different state-of-the-art networks (AlexNet, Vgg-19, and Inception-v3) are used in four different experiments. The different tissue labels (calcification, fibrosis, neovascularization, macrophage, intima, and media). The experiments are started with fine-tuning the networks, which is the most common way of applying pre-trained networks for various applications in the field of medical image analysis. Each experiment is designed based on the limitations of the previous experiment to achieve the main goal of this example, which defined as designing an accurate intracoronary tissue classification model using deep feature learning in an efficient procedure. The second experiment is performed to avoid convergence issues in fine-tuning the networks, overfitting by deep fine-tuning the networks, and training time. Deep features are very strong to describe arterial tissues and Random Forest works efficiently on large datasets with a very low risk of overfitting. Also, training process is considerably fast using Random Forest. But, when pre-trained networks are used as feature generators without fine-tuning, the classification results show lower accuracy, sensitivity, and specificity compared against using fine-tuned networks as classifiers. Majority voting on classification results of Random Forest classifiers can considerably improve the results of the second experiment without adding a huge computational burden. The accuracy, sensitivity, and specificity obtained from the third experiment (majority voting from Random Forest classification) can compete against the classification performance of the fine-tuned networks.

By evaluating the results of all the experiments, it is more efficient if pre-trained networks are used as feature extractors and train Random Forest for each set of generated features to perform the classification. Then, majority voting method provides the final tissue classification result. FIGS. 9A-F show classification results for each coronary artery tissue.

One goal of this example was to propose an approach for OCT imaging using deep feature learning from different CNN models and to evaluate their performance on a complex multi-class classification problem such as pathological formations in coronary artery tissues. The most significant outcome is to be able to automatically differentiate between intracoronary pathological formations observed from OCT imaging. This might be highly relevant for automatic assessment of coronary artery disease in KD. With the proper dataset and manual annotation, this might be adapted for adult coronary artery diseases to fully assess the structural information of the coronary artery. Majority voting from Random Forest classification using deep features have been successful in classifying coronary artery tissues. The final tissue labels were obtained with high accuracy, sensitivity, and specificity, which confirm the robustness of the technique proposed herein considering the high variability of pathological formations, OCT artifacts, and the small size of the arteries in pediatric patients, which is followed by very thin layers in coronary artery structure.

In this example, the relevance of deep features obtained using transfer learning for OCT imaging and the practical aspect of using RF classification to obtain the final decision in a clinically acceptable computational time have been outlined.

Example 2—Fully Automatic Diagnostic Model of Coronary Artery Lesions Using OCT Imaging IV-OCT is a light based imaging modality with high resolution, which employs near-infrared light to provide tomographic intracoronary images. Morbidity caused by CHD is a substantial cause of ACS and sudden cardiac death. The most common intracoronay complications caused by CAD are intimal hyperplasia, calcification, fibrosis, neovascularization, and macrophage accumulation, which require an efficient prevention strategies. OCT can provide discriminative information of the intracoronary tissues, which can be used to train a robust fully automatic tissue characterization model based on deep learning. This example aims to design a diagnostic model of coronary artery lesions. Particularly, a Random Forest was trained using CNN features to distinguish between normal and diseased arterial wall structure. Then, based on the structural variations of the arterial wall, a fully convolutional network is designed to extract the tissue layers in normal cases, and pathological tissues regardless of lesion type in pathological cases. Then, the type of the lesions can be characterized with high precision using models such as the one presented above. The results demonstrate the robustness of the model with the approximate overall accuracy up to 90%.

Coronary artery disease leads to progression of pathological formations in arterial wall layers, which may be followed by acute coronary syndrome. Considering the significant role of coronary arteries in functionality of cardiac tissues by controlling the blood flow to myocardium, coronary artery disease is recognized as the main cause of myocardial infarction and sudden death. The early mechanism, which leads to acute myocardial infarction is the formation of intracoronary pathological tissues and vulnerable coronary plaque rupture. This requires a high resolution imaging modality to be identified. Catheter based imaging modalities demonstrate higher resolution to visualize intracoronary structural information than non-invasive imaging techniques such as MR and CT. Intravascular ultrasound is widely used in cardiology to evaluate coronary artery tissue layers and pathological formations, but the low pullback speed and limited axial resolution of IVUS (100-150 µm) restricted its application to evaluate various cases with intimal hyperplasia, and pathological formations. Intracoronary OCT is recognized as a feasible and safe imaging technique with higher resolution of 10-15 µm than IVUS imaging, which can provide detailed structural tissue information. OCT is a catheter based invasive imaging modality, which employs a bandwidth in the near-infrared spectrum with central wavelength of approximately 1300 nm. Using such wavelength results in the tissue penetration of 1-3 mm. A single fiber-optic in OCT is responsible to emit the light and record the back-scattering of light from the arterial wall by simultaneous rotation, and pullback along the arterial wall. OCT works based on interferometry principal to measure the back-scattered signal since the direct measurements are impossible due to the high speed of light. OCT is significantly used in cardiology for diagnostic assessment of coronary atherosclerosis. As a limitation, light is strongly attenuated by blood as a result of light absorption by hemoglobin, and scattering by the red blood cells. Therefore, blood clearance is required during the imaging process.

Normal coronary artery has a three-layered structure. The outermost arterial wall, adventitia, is responsible to protect the arterial wall from over stretching and serves the mechanical connections with surrounding tissues. Adventitia is recognized as a signal rich pattern in OCT images. Media is the second arterial wall layer, which is composed of smooth muscle cells, elastic lamina, and collagen. Media is the most significant mechanical layer, which is visualized as a signal poor pattern in OCT images. Intima is the innermost arterial wall layer in direct contact with blood flow. Intima is composed of endothelial cells and it is recognized as a signal rich pattern in OCT images. Coronary arteries are responsible to deliver blood to the cardiac muscle, which supplies the required amount of oxygen and nutrients to the heart muscle. Therefore, coronary artery disease can be followed by serious implications. This can lead to myocardial infarction and sudden death. In 95% of patients with symptomatic coronary artery disease and intracoronary pathology, there is a risk of atherosclerosis. In the remaining 5% of the patients, there is a huge risk of inflammatory, degenerative or congenital diseases, which are serious cardiac complications. Therefore, evaluation of intracoronary tissues in acute phase of the disease is important to prevent myocardial infarction. Manual segmentation of the tissues in coronary artery images is tedious, time-consuming, and particularly error-prone from one observer to another and interpretation of the OCT images are highly challenging, even for a trained expert. Fully automatic method based on recent machine learning techniques, particularly deep learning, would have significant impact on efficient clinical diagnosis of coronary artery disease as a robust indicator of progression of pathological formations.

Optical coefficient approaches are used for intracoronary tissue characterization in some studies. Atherosclerotic plaque characterization is performed using attenuation and back-scattering coefficient from intracoronary OCT images.

Three different plaque types (fibrosis, lipid, and calcification) have been recognized by considering their attenuation coefficients. The plaque was also classified into two groups with high and low attenuation coefficients. This method was not robust to measure the back-scattering coefficient in the cases with the lack of intensity calibration. A tissue characterization model based on quantification of the attenuation coefficients at different penetration depths of intracoronary OCT images has been proposed. However, the multi-scattered signal was not considered in this example. In addition, the results for uniform-layered phantom does not show a good consistency. Evaluation of attenuation coefficient, back-scattering coefficient, and pixel-wise intensity in intracoronary OCT images are used to characterize various tissues. Moreover, various machine learning approaches are used for intracoronary tissue characterization. A model to characterize atherosclerotic plaques using Random Forest as the classifier exists. Combination of texture features and attenuation coefficients are used for plaque classification in intracoronary OCT images. A tissue characterization model is proposed using Random Forest as the classifier to discriminate between calcification, lipid, and fibrous plaques. A-line modeling method for plaque characterization has also been proposed. However, the effect of blood was not considered in this example.

Recently, deep learning was widely used in the field of medical imaging for various applications. Convolutional Neural Networks (CNNs) are recognized as the robust neural network architectures for classification tasks, where their output deep feature is a feature vector per image with an associated single class label predicted by the network. Since training a network from scratch requires a lot of data and considering the limited available data in the field of medical image analysis, it is efficient to use pre-trained networks by fine-tuning and transfer learning. Therefore, using the same architecture of the pre-trained network, the weights at each layer are initialized by the weights of the pre-trained network to start the iterative weight update by layer-wised fine-tuning to find the optimal parameters for one or more applications. A CNN based plaque characterization method has also been proposed, but the results d not show a good precision of the method to be used by clinicians. In another study, the performance of a CNN and an artificial neural network (ANN) is compared to characterize calcification, and lipid versus other tissues. However, all the pathological tissues and normal cases were not considered in this example.

A tissue characterization model with high precision to detect all coronary artery normal and pathological tissues automatically may not exist. A complete intracoronary tissue characterization model can be useful for clinicians for early detection of pathological tissues. Although optical properties of tissues and texture features can provide a fair description of tissues, but considering the challenges of the OCT images, detailed tissue information is required for better representation and evaluation of various arterial wall tissues. On the other hand, all the proposed tissue characterization models focused on characterizing a limited number or specific coronary artery lesions. There is no complete framework, which starts by evaluating the arterial wall structure to distinguish between normal structure of arterial wall and pathological cases, which the three-layered arterial wall structure is affected by coronary artery disease. There is no tissue characterization model, which can be extended to characterize all types of pathological formations.

Considering the strength of CNN features to describe various intracoronary tissues, a tissue characterization model was trained to discriminate between arterial wall tissue layers, intima and media, as well as pathological formations, specifically calcification, neovascularization, fibrosis, and macrophage accumulation. The final tissue characterization model was designed using CNNs as feature extractors from each tissue to train Random Forest (RF) as a classifier. Majority voting approach was used for final classification decision. The model is highly Precise to characterize various intracoronary tissues. In the example above, the main contribution was to find the features and classifier, which are reliable for intracoronary tissue characterization using OCT images. Therefore, the performance of various classifiers was assessed to design the model presented herein. In this example, it was aimed to design a computer aided diagnostic framework providing clinicians with an operator-independent diagnosis of coronary lesions. For this purpose, the following steps should be considered, which contribute to design a fully automatic tissue characterization model:

1. Pre-processing to remove the surrounding arterial wall tissues was performed on each frame of the OCT pullbacks by applying active contour and connected component approaches. First, the pre-processing steps are additional computational steps and second, designing a pre-processing approach, which can be generalized to all the cases, is very challenging. This can decrease the certainty level of the tissue characterization model, specifically in diseased coronary arteries. Considering the artifacts of the imaging system, and the small size of the arterial wall as well as the limitations of the traditional approaches. It is more efficient if the original images can be considered without applying any pre-processing step to assure that all the details of the tissues are considered in the analyses presented herein.

2. The OCT pullbacks with normal and diseased coronary artery were determined by expert cardiologist. To have a complete tissue characterization model, as the first step, it is very efficient if the model can recognize between normal and diseased arterial wall structure. Accordingly, it can look for arterial wall layers in the coronary arteries with normal three-layered structure and pathological formations in the coronary artery affected by disease.

3. The proposed model in Example 1 described above is a robust model for tissue characterization, which can discriminate between various types of pathological formations as well as the normal arterial wall layers with very high precision, which makes the model unique for clinical purposes. All the tissues were extracted using the ground-truth. However, to have a fully automatic tissue characterization model, all the tissues should be extracted automatically regardless of the tissue type. Then, the tissue characterization model can successfully discriminate between various pathological formations.

To address all the points mentioned above, first, applying the designed CNN model for tissue classification using small patches on the whole image was considered instead of extracting the ROIs and using the model as tissue characterization. However, the patch-based classification using CNNs has some limitations: 1. The network should be run for each patch separately, which results in redundant feature extraction process due to the overlapping patches. 2. The patch size selection is challenging since using small patches, the network considers a small context because of applying max-pooling. Using large patches may require more max-pooling steps, this can reduce the localization accuracy. 3. Considering the huge computational time, the pre-processing steps are required to remove the unnecessary tissues and reduce the processing time, which is an additional step. Also, an accurate pre-processing model, which can be generalized to all the cases is challenging by itself.

Fully convolutional networks (FCNs) are known as the delicate architectures, which can overcome the mentioned limitations of the patch-based classification using CNNs. FCNs can be trained on less number of training images with higher pixel-wised segmentation precision. In FCNs, the pooling operators are replaced by up-sampling operators to enhance the output resolution. The arbitrary size of the image can be fed to the network since there is no fully convolutional layer involved in the network architecture and the network is trained end-to-end, pixels-to-pixels to exceed the training process for an accurate segmentation. Therefore, the pre-processing is not necessary using FCNs since the training process is very fast, which does not require the additional step of unwanted tissue removal to exceed the training process. This may improve the tissue characterization model described in Example 1 by automatic extraction of ROIs using semantic segmentation.

Figure 10:
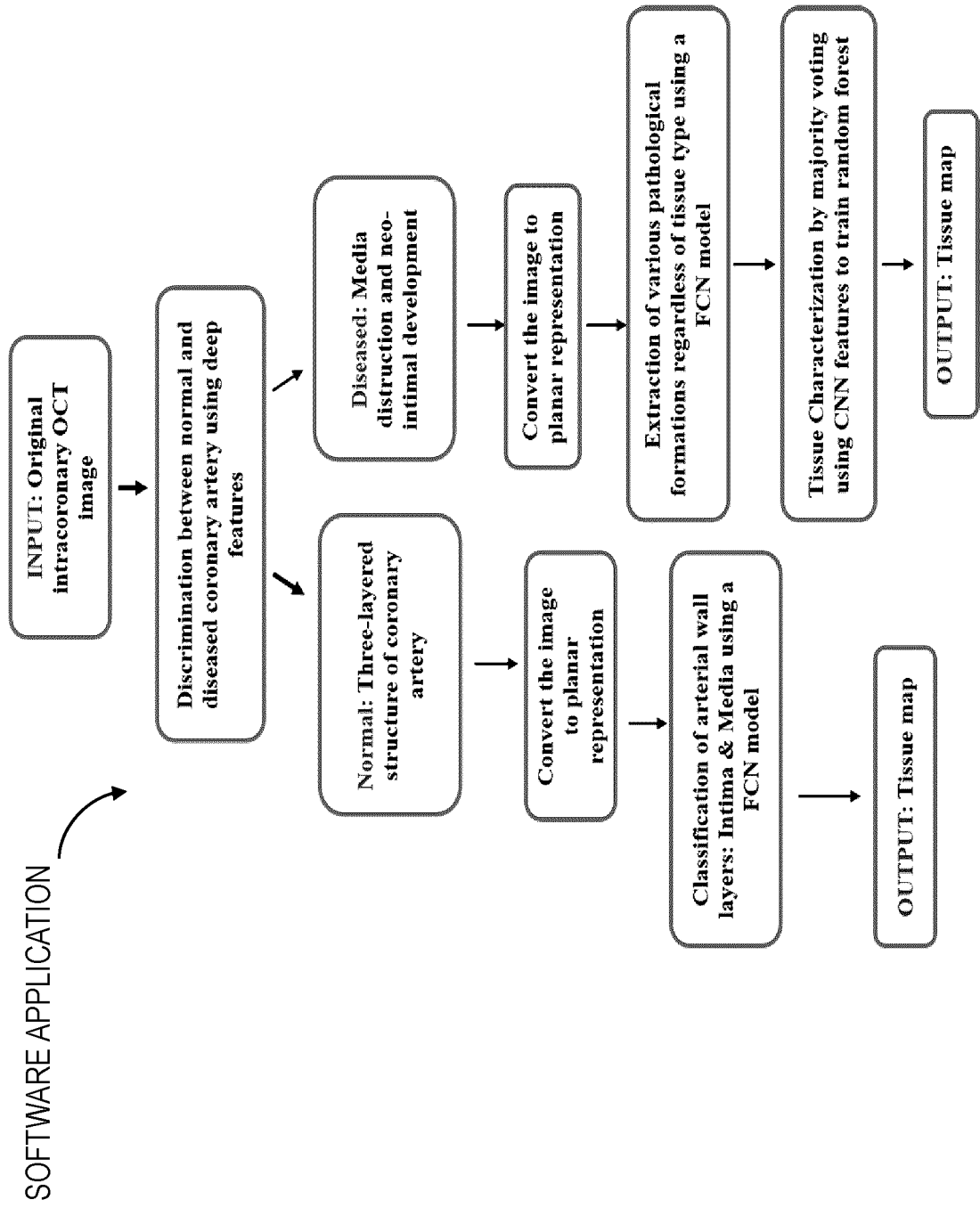
FIG. 10 is a schematic view of another example of a software application for determining a coronal artery tissue type for processing original intracoronary OCT images into output tissue map(s), in accordance with one or more embodiments.

Different steps of the tissue characterization model are shown in the flowchart of FIG. 10. Each step of this example is discussed in the following sections.

The experiments are performed on the total of 45 intracoronary OCT pullbacks obtained from patients with Kawasaki disease (KD). Image acquisition is performed using FD-OCT (St. Jude Medical Inc., St. Paul, Minnesota, USA) with the pullback speed of 20 mm/sec. The axial and lateral resolutions of the OCT system are 12-15 μm and 20-40 μm respectively. Each pullback consists of approximately 100 frames of DICOM images per patient. Permission to conduct this example on retrospective OCT studies was granted by the institutional review board. From the total of 45 OCT pullbacks, 26 pullbacks are considered as normal since the three-layered structure of the coronary artery is preserved although the arterial wall is affected by KD. The remaining OCT pullbacks are recognized as diseased due to neo-intimal development and formation of pathological tissues. Kawasaki disease (KD) is an inflammatory disease, which leads to inflammation in the walls of medium-sized arteries throughout the body. Although a high dose of Intravenous Immune Globulin (IVIG) infusion reduces the risk of coronary artery complications, about 5% of treated children, and 15% to 25% of untreated children suffer a risk of experiencing coronary artery aneurysms or ectasia. Intimal thickening, media disappearance, lamellar calcification, fibrosis, macrophage, and neovascularization are the most distinguished pathological features of late coronary artery lesions in Kawasaki disease. In severe cases, they can lead to myocardial infarction and sudden death.

Figures 11A, 11B:
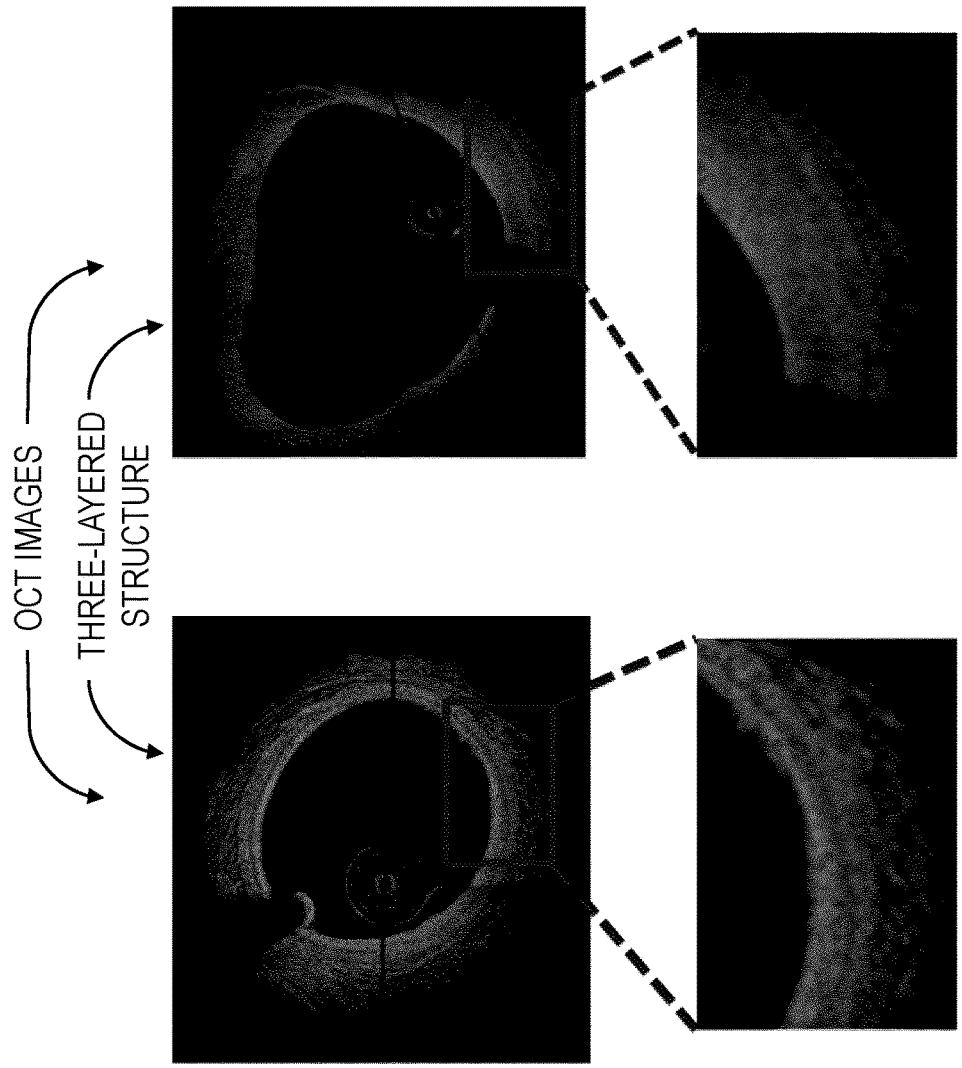
FIGS. 11A and 11B are OCT images showing structure of coronary artery including a three-layered structure with intima, media, adventitia, and surrounding tissues, with insets showing neo-intimal development and disappearance of the media layer, in accordance with one or more embodiments.

The first step of the intracoronary tissue characterization model is focused on discriminating between normal and diseased arterial wall structure. Normal structure refers to the three-layered structure of the arterial wall even if the artery is affected by a disease, the three-layered structure is preserved. The diseased arterial wall structure is referred to the neo-intimal development (FIG. 11). To discriminate between normal and diseased arterial wall structure, the features that a CNN learns were investigated.

Figure 12:
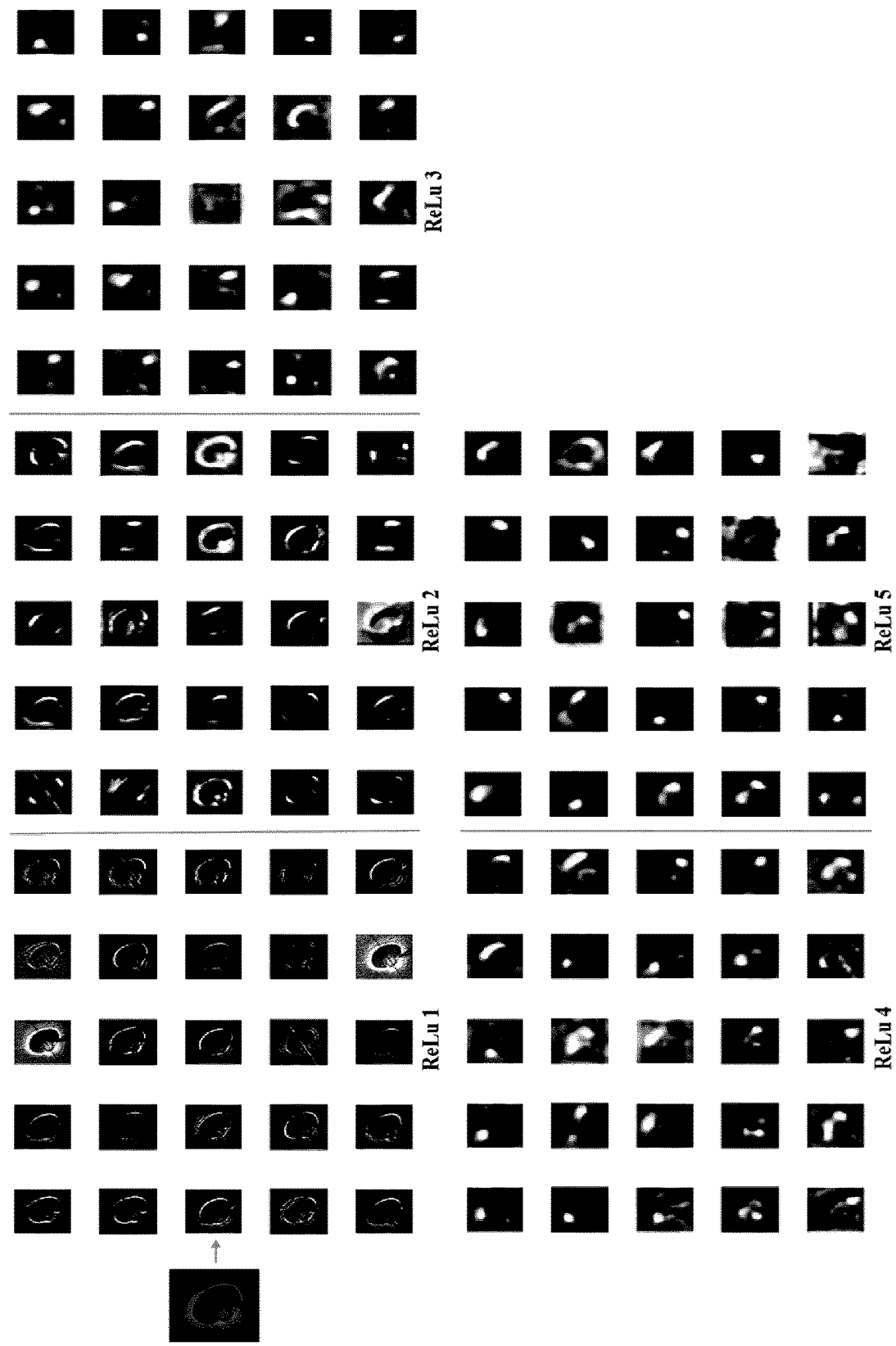
FIG. 12 shows a schematic view of the 25$^{th}$ strongest activations learned by AlexNet simple architecture network, with projection of features in pixel space for use in determining the general structural variations in arterial wall, in accordance with one or more embodiments.

Convolutional Neural Networks (CNNs) are developed on convolutional layers. These layers are responsible to excite features from the local receptive field of the input image. Therefore, convolutional layers are composed of shared weights between the nodes to extract the similar local attributes in the input channels by sliding the filters through the input image with defined step size, which is called stride. The extracted feature map from each convolutional layer is the input of the next layer. Using a non-saturating activation function, Rectified Linear Unit (ReLU), that replaces the negative values by zero in the feature map, which can accelerate the training process. In this step of the example, it is demonstrated that the features extracted from a simple CNN can successfully represent the general arterial wall structure to discriminate between the normal and diseased coronary artery segments. To compare the activations excited by each layer of the network with the original image, all the activations are projected to the input pixel space. Using the ReLU function, the positive activations are used to build the final feature map. Considering that the ReLU replaces negative values by zero, the white regions in FIG. 12 show the positive activations. The channels in each layer learn various activations. It is shown in FIG. 12 that the first layers learn and excite the abstract level information regarding the shape, corners, and edges of the original image, which can effectively capture information regarding the borders of different layers. Complex invariance by evaluating the texture information is recognized in deeper layers. This may determine the robustness of deep features to describe and evaluate the general structural differences between images to discriminate between normal and diseased frames in various OCT pullbacks. Therefore, Random Forest is trained using CNN features to classify between normal and diseased arterial wall structures. To generalize the model to all the cases, the features were extracted from each frame of OCT pullbacks. All the features and associated labels are considered as a single feature matrix. Then, the features were split into training and test sets by considering 75% of the feature vectors as the training features, and the remaining 25% of the features as the test features.

Figure 13:
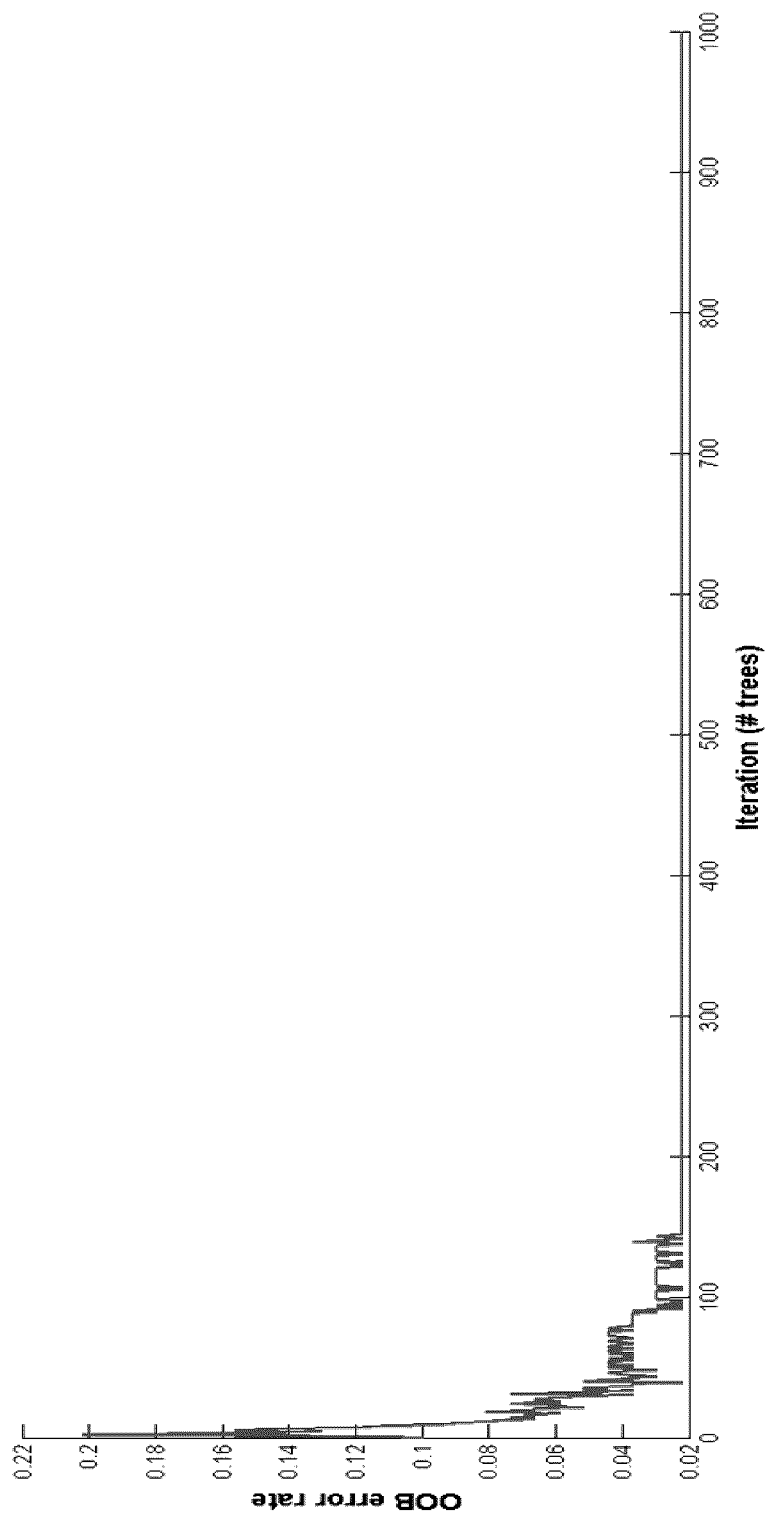
FIG. 13 is a graph showing OOB error rate as function of iterations during training of a classification engine to find an optimal number of trees of Random Forest, in accordance with one or more embodiments.

Therefore, in this step, AlexNet is used as feature generator to train Random Forest as a classifier to generally discriminate between normal and diseased images in each pullback. The number of trees is set to 145 by evaluating the performance of Random Forest using out of bag (OOB) error rate (FIG. 13) for 1000 of trees. Fewer number of trees reduces the training time of the Random Forest model. The number of randomly selected predictors (mtry) is set to 7.

Figure 16:
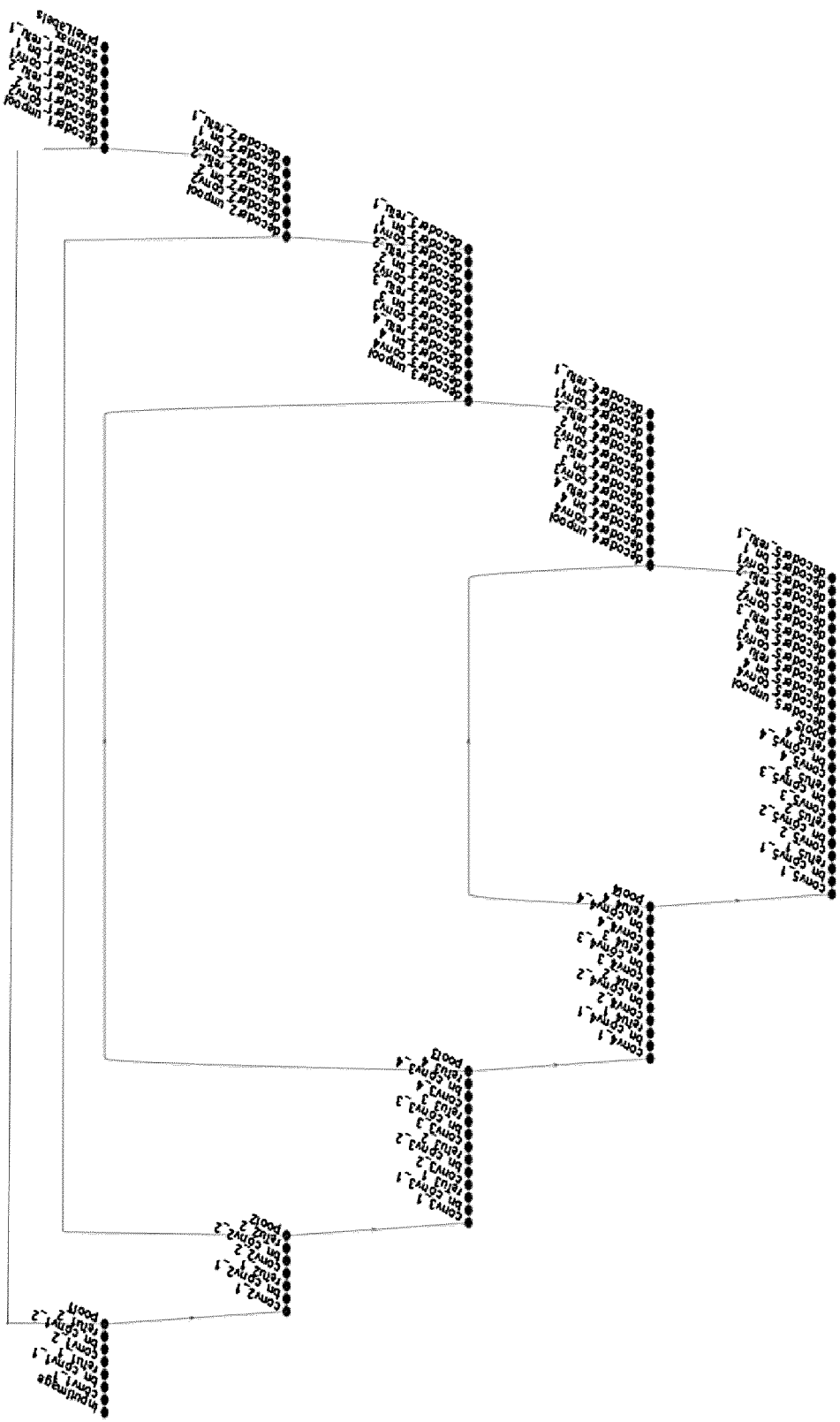
FIG. 16 is a schematic view of an architecture of the VGG-based FCN of FIG. 14, in accordance with one or more embodiments.

Generally, the network architecture used for semantic segmentation is composed of an encoder network followed by a decoder network. The encoder can be a pre-trained CNN. The decoder is responsible to project the learning features by the encoder from the feature space to the pixel space to get the dense classification. FCNs perform semantic segmentation by considering the context as well as each pixel localization in the images. Compared to CNNs, FCNs can take the image with an arbitrary size as an input, since there is no fully connected layer involved to restrict the input size. FCNs are built on locally connected convolution, pooling, and up-sampling layers. The network does not have any fully connected layer, which considerably reduce the number of parameters and training time. Considering the local connected layers in the network architecture, the network works independently from the original image size. The main parts of the FCNs are down-sampling path to extract the contextual information and the up-sampling path to recover the pixel localization. One of the standard networks, which is used as the basis of semantic segmentation is VGG architecture. VGG-19 is used in this example. Using VGG-based FCN, the knowledge is transferred from VGG-19 to perform semantic segmentation. The VGG-19 is used as the encoder of the FCN model. Fully connected layers are converted to fully convolutional layers using 1×1 convolution, which produce the feature map. Then, the up-sampling is started to convert the feature map from feature space to pixel space using transposed convolutions. Besides the deconvolutional layers, up-pooling is required as well. Considering that the max-pooling operation is non-invertible, the max location switches are recorded during max-pooling to approximately reconstruct the data from the above layer using the recorded positions. The learning parameters are set based on the optimal parameters found for fine-tuning in Example 1 (the momentum, and the scheduling rate are set to 0.9 and 0.95 respectively. The learning rates for all the convolutional layers are set to 0.01). Other significant factors, which determine the performance precision of FCNs are the choices of loss function and optimizer. The pathological formations represent a very small fraction of the cross-sectional coronary artery images, which causes the occurrence of a sever class imbalance. This results in sub-optimal performance of the network. To deal with the problem of class imbalance, Generalized Dice Loss (GDL) was chosen as the objective function, which is defined as follows, $$GDL = 1 - [2(\Sigma_l w_l \Sigma_n r_{ln} p_{ln})/(\Sigma_l w_l \Sigma_n r_{ln} + p_{ln})] \quad (7)$$

Where w is the weight assigned to each class with label I, n is the number of image from the total of N images, R demonstrate the ground-truth with the pixel value of r assigned to each label for the image n, and p is the probabilistic decision map for each class with label I. The weights demonstrate the contribution of each label in minimizing the loss function, which is defined as the inverse of the region size for foreground (the region of interest), and background (all the other tissues). This makes the model suitable to deal with the class imbalance problem. Adaptive momentum estimation (Adam) was selected for stochastic optimization, which uses the first order gradients with little memory requirement and fast convergence. FIG. 16 shows the architecture of VGG-based FCN used in this example.

Figure 14:
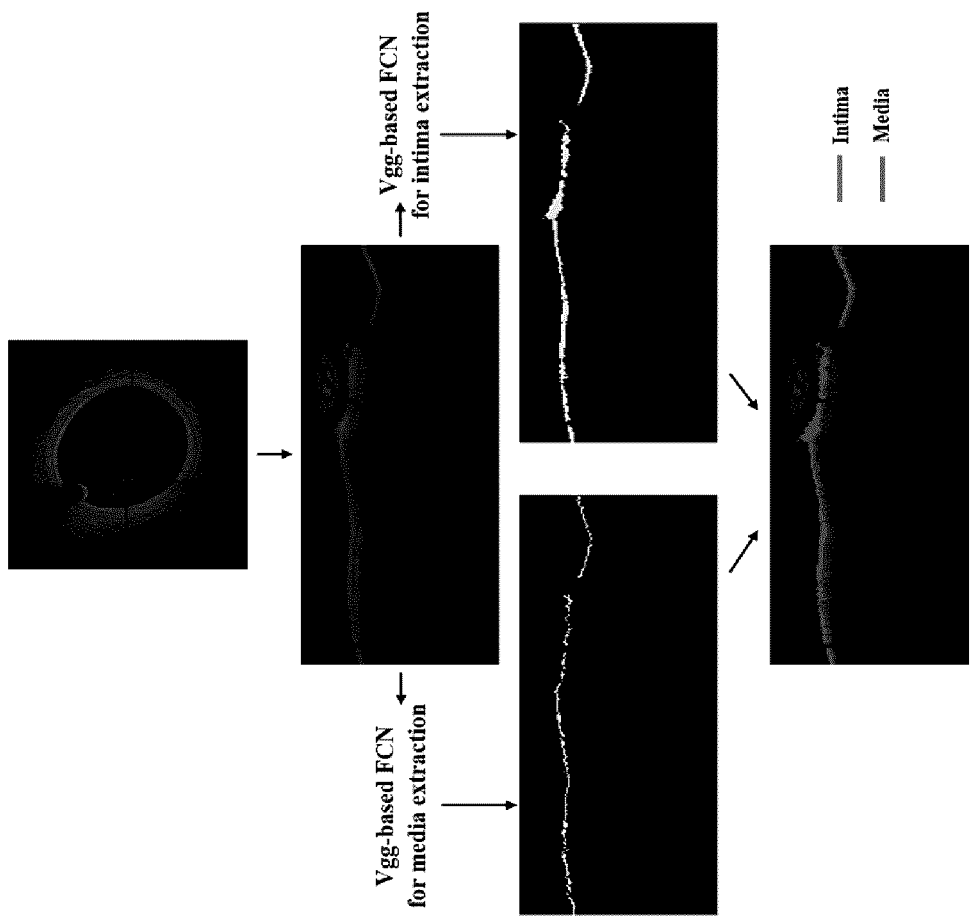
FIG. 14 is a schematic view of OCT images processed using an exemplary VGG-based FCN engine to segment intima and media layers, in accordance with one or more embodiments.

The experiments are performed on 26 various OCT pullbacks. All the frames at each pullback represent the coronary arterial wall with three-layered structure. Two VGG-based FCNs with the same structure explained in the previous section are trained in parallel to extract intima and media layers respectively. The first VGG-based FCN performs two class segmentation to extract intima layer versus all other tissues, and the second FCN takes the same frame of the pullback and simultaneously performs segmentation of the second layer, media, versus all other tissues. The segmentation result is combined as the final decision to extract intima and media layers. The steps of tissue layer detection is visually shown in FIG. 14. The images are categorized in three sets of training, validation, and test. The total of 85% of the images are selected for training and validation, and the remaining 15% of the images are considered as the test set.

Figure 15:
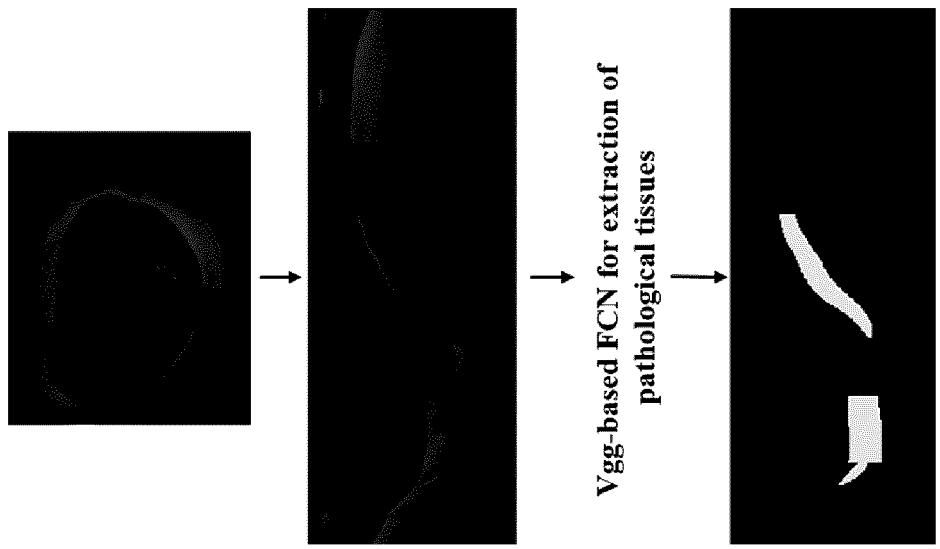
FIG. 15 is a schematic view of an example of the VGG-based FCN engine of FIG. 14 to detect pathological tissues, in accordance with one or more embodiments.

The experiments are performed on 19 different OCT pullbacks with pathological formations, such as calcification, neovascularization, fibrosis, and macrophage accumulation. The VGG-based FCN with the same structure shown in FIG. 16 is trained for two class segmentation of pathological tissues versus all other arterial wall tissues. Therefore, the output of the network is the detection of pathological tissues regardless of the tissue type. The steps of pathological tissue detection is visually shown in FIG. 15. This is an important step to make the previous tissue characterization model fully automatic since the model can discriminate between the pathological tissues accurately. The 85% of the images are selected as training and validation sets, and the remaining 15% is selected as the test set. When all the pathological tissues are extracted from the original image, CNNs are applied as feature extractors to train Random Forest as a classifier. The final classification is performed using majority voting approach.

TABLE 12

Measured accuracy, sensitivity, specificity, and BF-score for intima and media detection using FCN model.

| Tissues | Accuracy | Specificity | Sensitivity | BF-score |
|---|---|---|---|---|
| Intima | 0.90 ± 0.04 | 0.86 ± 0.06 | 0.93 ± 0.03 | 0.99 ± 0.01 |
| Media | 0.87 ± 0.04 | 0.82 ± 0.05 | 0.91 ± 0.02 | 0.99 ± 0.01 |

TABLE 13

Measured accuracy, sensitivity, specificity, and BF-score of pathological tissues detection using FCN model.

| | Accuracy | Specificity | Sensitivity | BF-score |
|---|---|---|---|---|
| Pathological | 0.96 ± 0.04 | 0.95 ± 0.05 | 0.97 ± 0.03 | 0.96 ± 0.04 |

The experiments are performed on the total of 45 intra-coronary OCT pullbacks obtained from patients with Kawasaki disease. The cross-sectional images of the 26 OCT pullbacks are recognized as the coronary artery segments with three-layered structure of the arterial wall, which are referred to as normal structures. The cross-sectional images of the remaining 19 OCT pullbacks are recognized as diseased coronary artery segments with neo-intimal development and formation of pathological tissues. For the first step, Random Forest is trained to evaluate the general structure of the arterial wall. The classification result is reported as measured accuracy, sensitivity, and specificity in Table 12. The result shows the robustness of CNN features to detect the general structural variances of arterial wall in normal and affected coronary arteries. All the feature vectors extracted from the pullback frames of different patients in both training and test sets are considered. Therefore, the model can be generalized to all the cases since the training and test sets are not restricted to a single patient with specific tissue attributes. As the next step, in normal cases, arterial wall layers (intima, and media) are detected. In pathological cases, the pathological tissues are extracted regardless of tissue type to feed them to the tissue characterization model to recognize the lesion type. For each segmentation result, the mean±std of the measurement is reported per class accuracy, specificity, and sensitivity of all the test set images in Table 13 for intima, and media detection and in Table 14 for extraction of pathological formations. FIGS. 17A-C include visual representations of the intima, and media detection for the frames of three different OCT pullbacks of various patients. FIGS. 18A-D include visual representations of the pathological tissue extraction for the frames of four different OCT pullbacks of various patients. The results show a high precision of the model to extract the pathological tissues, which is the most challenging and significant problem in coronary arteries affected by disease. To solve this problem, different factors are considered. First, all types of the pathological tissues are not present in all the frames of each pullback. In some cases, intima is thickened without the development of pathological tissues. In other cases, one, two, or more pathological tissues developed in the arterial wall layer may be present as a result of the disease. Second, the number of images, particularly in pathological cases, are very limited. Therefore, training a fully convolutional network to segment all the tissue types is not possible since the proposed model is not meant to be limited to a specific type of pathological formations and can be extended to all pathological lesions. Although the four most significant coronary artery complications caused by CAD were considered in this example, the model may be extended to all other pathological tissues even in human (e.g., adult, children, and elderly people) cardiology. Therefore, it may not be wise to train a single FCN model for each pathological tissue type separately since it is computationally very expensive and requires a huge memory. For this reason, it was decided to train a FCN, which can extract all the pathological tissues without considering the lesion type. Then, using the proposed tissue characterization model, extracting the CNN features, and training a Random Forest to distinguish between the tissue types demonstrated a very high precision.

TABLE 14

Measured accuracy, sensitivity, and specificity to evaluate general arterial wall structure.

|  | Accuracy | Specificity | Sensitivity |
|---|---|---|---|
| Normal structure | 0.94 | 0.96 | 0.91 |
| Diseased structure | 0.96 | 0.96 | 0.97 |

This example aimed to propose a fully automatic tissue characterization model, which can assist clinicians for better diagnosis of the coronary artery complications caused by coronary artery disease using OCT images. The complete tissue characterization model starts by evaluating the arterial wall tissue structure for each frame of the pullback to recognize between the normal three-layered structure of the arterial wall and neo-intimal development. Then, in normal cases, the model can detect the arterial wall layers, and in pathological cases, all the existing pathological formations can be extracted regardless of the tissue type using a FCN model. The extracted lesions can be categorized based on the lesion type using CNN features and majority voting on Random Forest decisions. Future work may be concentrated on evaluating the distensibility variations of the arterial wall tissues to assess the mechanical properties of the arterial wall using stationary OCT.

As can be understood, the examples described above and illustrated are intended to be exemplary only. For instance, in some embodiments, it might be preferred that the number of feature vectors or the number of feature extraction engines be an odd number. It is intended that in some embodiments the majority voting engine can be configured and adapted to determine the output coronal artery tissue type based on the preliminary coronal artery tissue types. However, in some other embodiments, the majority voting engine can be configured and adapted to determine the output coronal artery tissue type based on the preliminary coronal artery tissue types and also on some additional features including, without being limited to these examples, the shape of the lumen, different algorithms, annotations by clinicians, etc. In some embodiments, the FCNs can conveniently manage different input sizes of original OCT images. In these embodiments, the input sizes of the original OCT images inputted to the system and software application described herein can differ and still provide satisfactory output coronal artery tissue type and/or maps. Further, it is intended that the scope of this application encompass coronal artery tissue determination for all types of human patients including babies, children, adults and elderly people. The scope is indicated by the appended claims.

What is claimed is:

1. A system for determining a coronary artery tissue type, the system comprising:
   an optical coherence tomography (OCT) imaging system being configured for acquiring an OCT image of coronary artery tissue; and
   a controller having a memory and a processor configured to perform the steps of:
      accessing the OCT image;
      using a plurality of different feature extraction engines each being stored on the memory and being trained, extracting a corresponding plurality of different feature vectors comprising a plurality of features in at least a region of interest of the OCT image;
      using a plurality of classification engines each being stored on the memory and being trained, determining a corresponding plurality of preliminary coronary artery tissue types associated to the region of interest of the OCT image based on corresponding ones of the plurality of different feature vectors;
      using a majority voting engine stored on the memory and being trained, majority voting an output coronary artery tissue type associated to the region of interest of the OCT image based on the plurality of preliminary coronary artery tissue types; and
      outputting the output coronary artery tissue type.

2. The system of claim 1 wherein at least one of the plurality of different feature extraction engines has a fully convolutional network (FCN) architecture.

3. The system of claim 1 wherein at least one of the plurality of different feature extraction engines has a convolutional neural network (CNN) architecture.

4. The system of claim 3 wherein the CNN architecture of the one of the feature extraction engines is selected in the group consisting of: a simple architecture network, a deep architecture network and a complex architecture network.

5. The system of claim 1 wherein the plurality of different feature extraction engines comprises:
   a first feature extraction engine being stored on the memory and being trained, the first feature extraction engine being configured for extracting a first feature vector comprising a first plurality of features in the region of interest of the OCT image;
   a second feature extraction engine being stored on the memory and being trained, the second feature extraction engine being configured for extracting a second feature vector comprising a second plurality of features in the region of interest of the OCT image;
   a third feature extraction engine being stored on the memory and being trained, the third feature extraction engine being configured for extracting a third feature vector comprising a third plurality of features in the region of interest of the OCT image;
   the first feature extraction engine having a first architecture network, the second feature extraction engine having a second architecture network and the third feature extraction engine having a third architecture network, the first architecture network, the second architecture network and the third architecture network being different from one another.

6. The system of claim 5 wherein the first architecture network is provided in the form of an AlexNet simple architecture network, the second architecture network is provided in the form of a Vgg-19 deep architecture network and the third architecture network is provided in the form of an Inception-v3 complex architecture network.

7. The system of claim 5 wherein the plurality of classification engines comprises:
a first classification engine being stored on the memory and being trained, the first classification engine having been trained using feature vectors extracted using the first feature extraction engine;
a second classification engine being stored on the memory and being trained, the second classification engine having been trained using feature vectors extracted using the second feature extraction engine;
a third classification engine being stored on the memory and being trained, the third classification engine having been trained using feature vectors extracted using the third feature extraction engine.

8. The system of claim 1 wherein the plurality of classification engines are provided in the form of Random Forest classification engines.

9. The system of claim 1 wherein the plurality of classification engines have been trained using supervised learning during which each classification engine is trained to determine a preliminary coronary artery tissue type in a plurality of training OCT images each showing different coronary artery tissue types and having truth tissue type associated to each of the training OCT images.

10. The system of claim 1 wherein the majority voting engine is configured to provide an output indicating the output coronary artery tissue type on the OCT image, the output comprising overlaying at least one text string indicative of the determined output coronary artery tissue type on the OCT image.

11. The system of claim 1 further comprising an image conversion engine stored on the memory and being configured to convert the OCT image from a Cartesian representation to a polar representation.

12. The system of claim 1 wherein the output coronary artery tissue type is one of intima, media, adventitia, calcification, fibrosis, macrophage, neovascularization and scar.

13. The system of claim 1 further comprising an abnormality assessment engine configured to assess an abnormality associated to the region of interest of the OCT image based on the determined output coronary artery tissue type.

14. The system of claim 13 wherein the abnormality is one of coronary artery aneurysm, intima thickening, media border disappearance, thrombi and stenosis.

15. A computer-implemented method for determining a coronary artery tissue type, the method comprising:
using a controller having a memory and a processor:
receiving an optical coherence tomography (OCT) image of coronary artery tissue;
accessing the OCT image;
using a plurality of different feature extraction engines each being stored on the memory and being trained, extracting a corresponding plurality of different feature vectors comprising a plurality of features in at least a region of interest of the OCT image;
using a plurality of classification engines each being stored on the memory and being trained, determining a corresponding plurality of preliminary coronary artery tissue types associated to the region of interest of the OCT image based on corresponding ones of the plurality of different feature vectors;
using a majority voting engine stored on the memory and being trained, majority voting an output coronary artery tissue type associated to the region of interest of the OCT image based on the plurality of preliminary coronary artery tissue types; and
outputting the output coronary artery tissue type.

16. The computer-implemented method of claim 15 wherein at least one of the plurality of different feature extraction engines has a fully convolutional network (FCN) architecture.

17. The computer-implemented method of claim 15 wherein at least one of the plurality of different feature extraction engines has a convolutional neural network (CNN) architecture.

18. The computer-implemented method of claim 17 wherein the CNN architecture of the one of the feature extraction engines is selected in the group consisting of: a simple architecture network, a deep architecture network and a complex architecture network.

19. The computer-implemented method of claim 15 wherein the plurality of different feature extraction engines comprises:
a first feature extraction engine being stored on the memory and being trained, the first feature extraction engine being configured for extracting a first feature vector comprising a first plurality of features in the region of interest of the OCT image;
a second feature extraction engine being stored on the memory and being trained, the second feature extraction engine being configured for extracting a second feature vector comprising a second plurality of features in the region of interest of the OCT image;
a third feature extraction engine being stored on the memory and being trained, the third feature extraction engine being configured for extracting a third feature vector comprising a third plurality of features in the region of interest of the OCT image;
the first feature extraction engine having a first architecture network, the second feature extraction engine having a second architecture network and the third feature extraction engine having a third architecture network, the first architecture network, the second architecture network and the third architecture networks being different from one another.

20. The computer-implemented method of claim 19 wherein the first architecture network is provided in the form of an AlexNet simple architecture network, the second architecture network is provided in the form of a Vgg-19 deep architecture network and the third architecture network is provided in the form of an Inception-v3 complex architecture network.

* * * * *